US008795359B2

(12) United States Patent
Boyden et al.

(10) Patent No.: US 8,795,359 B2
(45) Date of Patent: *Aug. 5, 2014

(54) BREAST IMPLANT WITH REGIONALIZED ANALYTE SENSORS AND INTERNAL POWER SOURCE

(75) Inventors: Edward S. Boyden, Chestnut Hill, MA (US); Gregory J. Della Rocca, Columbia, MO (US); Daniel Hawkins, Pleasanton, CA (US); Roderick A. Hyde, Redmond, WA (US); Robert Langer, Newton, MA (US); Eric C. Leuthardt, St. Louis, MO (US); Terence Myckatyn, St. Louis, MO (US); Parag Jitendra Parikh, St. Louis, MO (US); Dennis J. Rivet, Chesapeake, VA (US); Joshua S. Shimony, St. Louis, MO (US); Michael A. Smith, Phoenix, AZ (US); Elizabeth A. Sweeney, Seattle, WA (US); Clarence T. Tegreene, Mercer Island, WA (US)

(73) Assignee: Elwha LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/495,299

(22) Filed: Jun. 13, 2012

(65) Prior Publication Data
US 2013/0338772 A1 Dec. 19, 2013

(51) Int. Cl.
*A61F 2/12* (2006.01)
(52) U.S. Cl.
USPC .......................................................... 623/8
(58) Field of Classification Search
USPC .......................................... 623/7–8
See application file for complete search history.

(56) References Cited

U.S. PATENT DOCUMENTS

| 3,124,136 | A | * | 3/1964 | Usher ........................... 606/213 |
| 3,559,214 | A | | 2/1971 | Pangman |
| 3,941,135 | A | | 3/1976 | von Sturm et al. |
| 4,384,288 | A | | 5/1983 | Walton |
| 5,207,709 | A | * | 5/1993 | Picha ........................ 623/23.74 |
| 5,270,163 | A | | 12/1993 | Gold et al. |
| 5,338,625 | A | | 8/1994 | Bates et al. |

(Continued)

FOREIGN PATENT DOCUMENTS

| BR | 9300601 | * | 10/1994 |
| CA | 2301445 | * | 2/2005 |
| WO | WO 2010/022130 A1 | | 2/2010 |

OTHER PUBLICATIONS

U.S. Appl. No. 13/495,310, Boyden et al.

(Continued)

*Primary Examiner* — Suzette J Gherbi

(57) ABSTRACT

Breast implants including sensor modules and related methods are described herein. Breast implants include those with: a shell configured to be substantially filled with a viscous material; a plurality of projections extending from an external surface of the shell, the projections forming a plurality of compartments adjacent to the external surface of the shell; at least one fluid-permeable cover attached to the projections, the cover completely enveloping the shell and the plurality of projections; a plurality of sensor modules attached to the shell, each of the sensor modules oriented to detect one or more analytes in a fluid within one of the plurality of compartments, wherein each of the plurality of sensor modules includes a unique identifier; and at least one power source operably attached to the plurality of sensor modules.

40 Claims, 14 Drawing Sheets

(56) References Cited

U.S. PATENT DOCUMENTS

| | | | |
|---|---|---|---|
| 5,475,096 A | | 12/1995 | Gold et al. |
| 5,564,439 A | * | 10/1996 | Picha .................. 604/890.1 |
| 5,668,267 A | | 9/1997 | Watson et al. |
| 5,797,898 A | | 8/1998 | Santini, Jr. et al. |
| 5,800,529 A | | 9/1998 | Brauker et al. |
| 5,833,603 A | * | 11/1998 | Kovacs et al. ................. 600/317 |
| 5,855,889 A | | 1/1999 | Watson et al. |
| 5,922,836 A | | 7/1999 | Watson et al. |
| 5,968,754 A | | 10/1999 | Watson et al. |
| 5,997,574 A | * | 12/1999 | Hayes et al. .................. 424/422 |
| 6,004,756 A | | 12/1999 | Watson et al. |
| 6,119,028 A | | 9/2000 | Schulman et al. |
| 6,304,766 B1 | | 10/2001 | Colvin, Jr. |
| 6,420,622 B1 | | 7/2002 | Johnston et al. |
| 6,477,395 B2 | | 11/2002 | Schulman et al. |
| 6,566,072 B1 | | 5/2003 | Watson et al. |
| 6,677,428 B1 | | 1/2004 | Watson et al. |
| 6,743,581 B1 | | 6/2004 | Vo-Dinh |
| 7,006,858 B2 | | 2/2006 | Silver et al. |
| 7,055,754 B2 | | 6/2006 | Forster |
| 7,129,166 B2 | | 10/2006 | Speakman |
| 7,215,976 B2 | | 5/2007 | Brideglall |
| 7,223,237 B2 | | 5/2007 | Shelchuk |
| 7,236,821 B2 | | 6/2007 | Cates et al. |
| 7,302,289 B2 | | 11/2007 | Crowley |
| 7,364,592 B2 | | 4/2008 | Carr-Brendel et al. |
| 7,410,616 B2 | | 8/2008 | Santini, Jr. et al. |
| 7,411,505 B2 | | 8/2008 | Smith et al. |
| 7,479,886 B2 | | 1/2009 | Burr |
| 7,485,345 B2 | | 2/2009 | Renn et al. |
| 7,577,470 B2 | | 8/2009 | Shah et al. |
| 7,641,688 B2 | | 1/2010 | Lesh |
| 7,709,134 B2 | | 5/2010 | Minteer et al. |
| 7,951,605 B2 | | 5/2011 | Pitner et al. |
| 7,964,390 B2 | | 6/2011 | Rozakis et al. |
| 8,043,373 B2 | | 10/2011 | Schuessler et al. |
| 8,070,808 B2 | | 12/2011 | Maxwell et al. |
| 8,138,005 B2 | | 3/2012 | Jang et al. |
| 8,145,434 B2 | | 3/2012 | Shachar et al. |
| 8,167,836 B2 | | 5/2012 | Lee et al. |
| 8,230,865 B2 | | 7/2012 | Shalon |
| 8,518,031 B2 | | 8/2013 | Boyden et al. |
| 2002/0010514 A1 | * | 1/2002 | Burg et al. ................. 623/23.75 |
| 2003/0074084 A1 | * | 4/2003 | Nakao ......................... 623/23.67 |
| 2003/0099682 A1 | * | 5/2003 | Moussy et al. ................ 424/423 |
| 2005/0143787 A1 | | 6/2005 | Boveja et al. |
| 2006/0034731 A1 | | 2/2006 | Lewis et al. |
| 2006/0069403 A1 | * | 3/2006 | Shalon et al. .................. 606/192 |
| 2006/0161253 A1 | * | 7/2006 | Lesh .................................. 623/8 |
| 2007/0077265 A1 | | 4/2007 | Klueh et al. |
| 2007/0106332 A1 | | 5/2007 | Denker et al. |
| 2007/0114138 A1 | | 5/2007 | Krasteva et al. |
| 2007/0128420 A1 | | 6/2007 | Maghribi |
| 2008/0160384 A1 | | 7/2008 | Iqbal et al. |
| 2008/0188836 A1 | | 8/2008 | Weber et al. |
| 2008/0300660 A1 | | 12/2008 | John |
| 2009/0012372 A1 | * | 1/2009 | Burnett et al. ................. 600/300 |
| 2009/0182426 A1 | | 7/2009 | Von Arx et al. |
| 2009/0254179 A1 | | 10/2009 | Burnett |
| 2009/0298704 A1 | | 12/2009 | Anwar et al. |
| 2009/0318802 A1 | | 12/2009 | Boyden et al. |
| 2010/0065097 A1 | | 3/2010 | Hyde et al. |
| 2010/0070002 A1 | | 3/2010 | Hyde et al. |
| 2010/0070003 A1 | | 3/2010 | Hyde et al. |
| 2010/0072994 A1 | | 3/2010 | Lee et al. |
| 2010/0269837 A1 | * | 10/2010 | Levinson et al. ............. 128/899 |
| 2010/0276302 A1 | | 11/2010 | Raguse et al. |
| 2010/0331634 A1 | | 12/2010 | Müller et al. |
| 2011/0044694 A1 | | 2/2011 | Scherer et al. |
| 2011/0077736 A1 | | 3/2011 | Rofougaran |
| 2011/0082356 A1 | | 4/2011 | Yang et al. |
| 2011/0098576 A1 | | 4/2011 | Hollstien |
| 2011/0137244 A1 | * | 6/2011 | Lee et al. .................. 604/103.02 |
| 2011/0208302 A1 | | 8/2011 | Glicksman |
| 2011/0250510 A1 | | 10/2011 | Cinquin et al. |
| 2011/0257494 A1 | | 10/2011 | Glazier et al. |
| 2011/0257623 A1 | | 10/2011 | Marshall et al. |
| 2011/0270028 A1 | * | 11/2011 | Honaryar ........................ 600/37 |
| 2011/0282444 A1 | | 11/2011 | Liu et al. |
| 2012/0302874 A1 | * | 11/2012 | Hollstien ...................... 600/424 |
| 2013/0190870 A1 | * | 7/2013 | Padsalgikar ...................... 623/8 |

OTHER PUBLICATIONS

U.S. Appl. No. 13/495,288, Boyden et al.
U.S. Appl. No. 13/495,275, Boyden et al.
U.S. Appl. No. 13/495,252, Boyden et al.
U.S. Appl. No. 13/495,212, Boyden et al.
PCT International Search Report; International App. No. PCT/US2013/045212; Jan. 8, 2014; pp. 1-5.
PCT International Search Report; International App. No. PCT/US2013/045206; Jan. 7, 2014; pp. 1-6.

* cited by examiner

BREAST IMPLANT WITH REGIONALIZED ANALYTE SENSORS AND INTERNAL POWER SOURCE

CROSS-REFERENCE TO RELATED APPLICATIONS

The present application is related to the following listed application(s) (the "Related Applications"). All subject matter of the Related Applications and of any and all parent, grandparent, great-grandparent, etc. applications of the Related Applications, is incorporated herein by reference to the extent such subject matter is not inconsistent herewith.

RELATED APPLICATIONS

U.S. patent application Ser. No. 13/495,212, entitled BREAST IMPLANT WITH ANALYTE SENSORS AND INTERNAL POWER SOURCE, naming Edward S. Boyden, Gregory J. Della Rocca, Daniel Hawkins, Roderick A. Hyde, Robert Langer, Eric C. Leuthardt, Terence Myckatyn, Parag Jitendra Parikh, Dennis J. Rivet, Joshua S. Shimony, Michael A. Smith, Elizabeth A. Sweeney and Clarence T. Tegreene as inventors, filed 13 Jun. 2012.

U.S. patent application Ser. No. 13/495,252, entitled BREAST IMPLANT WITH ANALYTE SENSORS RESPONSIVE TO EXTERNAL POWER SOURCE, naming Edward S. Boyden, Gregory J. Della Rocca, Daniel Hawkins, Roderick A. Hyde, Robert Langer, Eric C. Leuthardt, Terence Myckatyn, Parag Jitendra Parikh, Dennis J. Rivet, Joshua S. Shimony, Michael A. Smith, Elizabeth A. Sweeney and Clarence T. Tegreene as inventors, filed 13 Jun. 2012.

U.S. patent application Ser. No. 13/495,275, entitled BREAST IMPLANT WITH COVERING, ANALYTE SENSORS AND INTERNAL POWER SOURCE, naming Edward S. Boyden, Gregory J. Della Rocca, Daniel Hawkins, Roderick A. Hyde, Robert Langer, Eric C. Leuthardt, Terence Myckatyn, Parag Jitendra Parikh, Dennis J. Rivet, Joshua S. Shimony, Michael A. Smith, Elizabeth A. Sweeney and Clarence T. Tegreene as inventors, filed 13 Jun. 2012.

U.S. patent application Ser. No. 13/495,288, entitled BREAST IMPLANT WITH COVERING AND ANALYTE SENSORS RESPONSIVE TO EXTERNAL POWER SOURCE, naming Edward S. Boyden, Gregory J. Della Rocca, Daniel Hawkins, Roderick A. Hyde, Robert Langer, Eric C. Leuthardt, Terence Myckatyn, Parag Jitendra Parikh, Dennis J. Rivet, Joshua S. Shimony, Michael A. Smith, Elizabeth A. Sweeney and Clarence T. Tegreene as inventors, filed 13 Jun. 2012.

U.S. patent application Ser. No. 13/495,310, entitled BREAST IMPLANT WITH REGIONALIZED ANALYTE SENSORS RESPONSIVE TO EXTERNAL POWER SOURCE, naming Edward S. Boyden, Gregory J. Della Rocca, Daniel Hawkins, Roderick A. Hyde, Robert Langer, Eric C. Leuthardt, Terence Myckatyn, Parag Jitendra Parikh, Dennis J. Rivet, Joshua S. Shimony, Michael A. Smith, Elizabeth A. Sweeney and Clarence T. Tegreene as inventors, filed 13 Jun. 2012.

SUMMARY

In some aspects, a breast implant includes but is not limited to: a shell configured to be substantially filled with a viscous material; a plurality of projections extending from an external surface of the shell, the projections forming a plurality of compartments adjacent to the external surface of the shell; at least one fluid-permeable cover attached to the projections, the cover completely enveloping the shell and the plurality of projections; a plurality of sensor modules attached to the shell, each of the sensor modules oriented to detect one or more analytes in a fluid within one of the plurality of compartments, wherein each of the plurality of sensor modules includes a unique identifier; and at least one power source operably attached to the plurality of sensor modules. In some aspects, a breast implant includes but is not limited to: a shell configured to be substantially filled with a viscous material; a plurality of projections extending from an external surface of the shell, the projections forming a plurality of compartments adjacent to the external surface of the shell; at least one fluid-permeable cover attached to the projections, the cover completely enveloping the shell and the plurality of projections; a plurality of sensor modules attached to the shell, each of the sensor modules oriented to detect one or more analytes in a fluid within one of the plurality of compartments, wherein each of the plurality of sensor modules includes a unique identifier; at least one processor operably attached to the plurality of sensor modules; and at least one power source operably attached to the at least one processor. In some aspects, a breast implant includes but is not limited to: a shell configured to be substantially filled with a viscous material; a plurality of projections extending from an external surface of the shell, the projections forming a plurality of compartments adjacent to the external surface of the shell; at least one fluid-permeable cover attached to the projections, the cover completely enveloping the shell and the plurality of projections; a plurality of sensor modules attached to the shell, each of the sensor modules oriented to detect one or more analytes in a fluid within one of the plurality of compartments, wherein each of the plurality of sensor modules includes a unique identifier; at least one processor operably attached to the plurality of sensor modules; at least one power source operably attached to the at least one processor; and a transmission unit operably attached to the at least one processor. In some aspects, a breast implant includes but is not limited to: a shell configured to be substantially filled with a viscous material; a plurality of projections extending from an external surface of the shell, the projections forming a plurality of compartments adjacent to the external surface of the shell; a plurality of sensor modules attached to the shell, each of the sensor modules oriented to detect one or more analytes in a fluid within one of the plurality of compartments, wherein each of the plurality of sensor modules includes a unique identifier; and at least one power source operably attached to the plurality of sensor modules. In some aspects, a breast implant includes but is not limited to: a shell configured to be substantially filled with a viscous material; a plurality of projections extending from an external surface of the shell, the projections forming a plurality of compartments adjacent to the external surface of the shell; a plurality of sensor modules attached to the shell, the sensor modules configured to detect one or more biological analytes arising from biological tissue, the fluid within one of the plurality of compartments; at least one transmission unit attached to the plurality of sensor modules; and at least one power source attached to the plurality of sensor modules and to the transmission unit. In addition to the foregoing, other device and system aspects are described in the claims, drawings, and text forming a part of the present disclosure.

In one aspect, a method of monitoring information from a breast implant includes but is not limited to: receiving first information from a first sensor module attached to a shell of a breast implant within an individual, wherein the first information includes a first unique sensor module identifier and sensor data from the first sensor module; receiving second information from a second sensor module attached to the shell of the breast implant within the individual, wherein the second information includes a second unique sensor module identifier and sensor data from the second sensor module; forming an initial record from the first information and the second information; calculating deviation limits regarding the initial record; setting deviation parameters based on the deviation limits and a predetermined set of standards; saving the initial record and the deviation parameters in memory in a computing device; receiving third information from the first sensor module attached to the shell of the breast implant within the individual, wherein the third information includes the first unique sensor module identifier and sensor data from the first sensor module; receiving fourth information from the second sensor module attached to the shell of the breast implant within the individual, wherein the fourth information includes the second unique sensor module identifier and sensor data from the second sensor module; updating the initial record with the third information and the fourth information; saving the updated record in memory in the computing device; comparing the updated record to the initial record and to the deviation parameters; and indicating if the updated record is within the deviation parameters of the initial record. In one aspect, a method of monitoring information from a breast implant includes but is not limited to: sending a signal from a transmission unit attached to one or more sensor modules attached to a breast implant in vivo, wherein the signal contains information regarding the detection of one or more biological analytes by the one or more sensor modules. In one aspect, a method of monitoring information from a breast implant includes but is not limited to: sending, from a remote device, a query signal to at least one transmission unit attached to a breast implant in vivo, the at least one transmission unit attached to one or more sensor modules configured to detect biological analytes in fluid from biological tissue; receiving, from a remote device, a response signal from the at least one transmission unit attached to the breast implant, the response signal including information from the one or more sensor modules; processing, in a computing device, the response signal to identify information from the one or more sensor modules; and identifying, for each of the one or more sensor modules, a detection result and a unique identifier. In one aspect, a method of monitoring information from a breast implant includes but is not limited to: sending a signal from at least one transmission unit attached to a breast implant in vivo, the signal including information regarding one or more sensor modules configured to detect biological analytes in fluid from biological tissue, the at least one transmission unit attached to the one or more sensor modules; receiving, from a remote device, a response signal from the at least one transmission unit attached to the breast implant, the response signal including information from the one or more sensor modules; processing, in a computing device, the response signal to identify information from the one or more sensor modules; and identifying, for each of the one or more sensor modules, a detection result and a unique identifier. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In addition to the foregoing, various other device, method and system aspects are set forth and described in the teachings such as text (e.g., claims and detailed description) and drawings of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
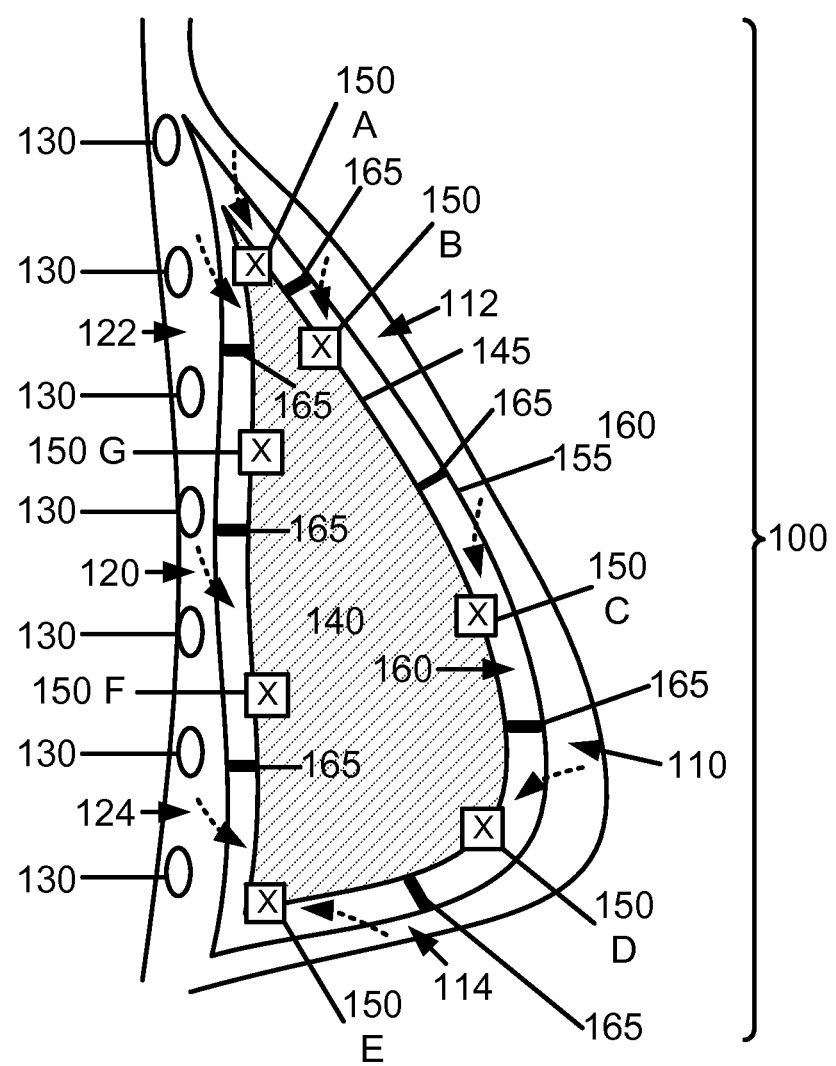
FIG. 1 is a schematic of a breast implant in vivo.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein.

The use of the same symbols in different drawings typically indicates similar or identical items.

With reference now to FIG. 1, shown is an example of a breast implant in vivo that may serve as a context for introducing one or more devices and processes described herein. The breast implants and related systems and methods described herein can be utilized in breast augmentation (e.g. for cosmetic purposes) as well as in breast reconstruction (e.g. after mastectomy or lumpectomy). The breast implants and related systems and methods described herein can be utilized in a low-profile implant device, for example configured for use after lumpectomy or in a male patient. FIG. 1 illustrates a breast implant 140 in vivo within an individual person's body. FIG. 1 shows a cross-section view through the side of a person, including a cross-section of the individual's ribs 130 in the chest wall 122, 120, 124. FIG. 1 depicts a cross-section view of the breast implant 140 in situ within a breast 100. The breast implant 140 includes a shell 145 configured to be substantially filled with a viscous material. The viscous material can be selected for a combination of non-toxicity as well as to provide structural support to the surrounding tissue while maintaining a natural feel. For example, the viscous material can include saline or a silicone gel. The breast implant 140 includes a fluid-permeable cover 155, the cover completely enveloping the shell 145. As illustrated in FIG. 1, there is a gap 160 between the fluid-permeable cover 155 and the shell 145. A series of projections 165 extend from the external surface of the shell 145. The projections 165 are located between the sensor modules 150 on the surface of the shell 145. As illustrated in FIG. 1, the projections 165 are positioned on the on the surface of the shell 145 to form a compartment around each of the sensor modules 150. The projections 165 form a plurality of compartments adjacent to the external surface of the shell 145 within the gap 160. The series of projections 165 extend from the external surface of the shell 145 to the fluid-permeable cover 155 and are attached to both the external surface of the shell 145 to a surface of the fluid-permeable cover 155. Some embodiments include a cover 155 configured to completely envelop the shell 145 with a uniform gap 160 between the cover 155 and the shell 145, wherein the projections 165 are approximately the same height as the width of the gap 160.

The breast implant 140 includes a plurality of sensor modules 150 A, B, C, D, E, F and G. Each of the sensor modules 150 A, B, C, D, E, F and G is attached to the shell 145 and oriented to detect one or more analytes in a fluid within one of the plurality of compartments adjacent the shell 145. The compartments are configured to allow for fluid flow from the adjacent tissue into the compartments through the fluid-permeable cover 155, as illustrated in FIG. 1 by the dotted arrows. The sensor module 150 located within each compartment is oriented to detect analytes in the fluid from the adjacent tissue. Each sensor module is positioned to detect one or more analytes in fluid from tissue in its surrounding regions. For example, sensor module 150 C is oriented to detect one or more analytes in fluid from tissue in its surrounding regions, identified in FIG. 1 as 112 and 110. Also by way of example, sensor module 150 D is oriented to detect one or more analytes in fluid from tissue in its surrounding regions, identified in FIG. 1 as 110 and 114. As another example, sensor module 150 E is oriented to detect one or more analytes in fluid from tissue in its surrounding regions, identified in FIG. 1 as 114 and 124. Also for example, sensor module 150 F is oriented to detect one or more analytes in fluid from tissue in its surrounding regions, identified in FIG. 1 as 120 and 124. Also by way of example, sensor module 150 G is oriented to detect one or more analytes in fluid from tissue in its surrounding regions, marked 120 and 122.

The term "analytes," as used herein, includes biological analytes arising from biological tissue. Analytes can be indicative of neoplasia in breast tissue. Analytes can be detected by the sensor modules described herein. For example, analytes include proteins, polypeptides, peptides, nucleic acids, polysaccharides, lipids, saccharides, oligosaccharides, glycoproteins, glycolipids, and proteoglycans. In some embodiments, analytes can include lipid-protein combinations, anchored proteins, lipoproteins, proteolipids and fatty acids. The specific analyte or analytes detected by a particular implant system depend on the sensor modules employed in that embodiment. In particular, analytes of interest include those that are indicative of abnormal cellular growth (e.g., neoplasms, malignancies, metastases, cancer) in or proximate to the breast although analytes can also indicate other cellular changes of medical interest in breast tissue. For example, analytes can include those indicative of the presence of breast cancer, the progression of breast cancer, or the initiation of breast cancer. For example, analytes can include those indicative of the presence of metastatic breast cancer and the translocation of breast cancer cells. For example, genetic amplification of the Her-2/neu oncogene is associated with some metastatic breast cancers, and analytes associated therewith include regions of the extracellular domain of the Her-2/neu protein (see Chourb et al., "Enhanced Immunodetection of Shed Extracellular Domain of Her-2/neu," Science Research 1(4): 325-329 (2009), which is incorporated herein by reference). For example, some matrix metalloproteinases have been shown to be markers for breast cancers (see Roy et al., "Matrix Metalloproteinases as Novel Biomarkers and Potential Therapeutic Targets in Human Cancer," Journal of Clinical Oncology, 27(31): 5287-5297 (2009), which is incorporated herein by reference). For example, analytes can include cancer markers such as calreticulin, cellular retinoic acid-binding protein II, chloride intracellular channel protein 1, EF-1-beta, galectin 1, peroxiredoxin-2, platelet-derived endothelial cell growth factor, protein disulfide isomerase and ubiquitin carboxyl-terminal hydrolase 5 (see Gromov et al., "Up-regulated Proteins in the Fluid Bathing the Tumour Cell Microenvironment as Potential Serological Markers for Early Detection of Cancer of the Breast," Molecular Oncology 4: 65-89 (2010), which is incorporated herein by reference). For example, an analyte can include cancer antigen 15-3 (CA 15-3) (see Chourb et al., "Improved Detection of the MUC1 Cancer Antigen CA 15-3 by ALYGNSA Fluorimmunoassay," Science Research 3(8): 524-528 (2011), which is incorporated herein by reference). An analyte can include circulating microRNAs. For example, circulating microRNAs have been found that are indicative of breast cancer cells (see Vilaamil et al., "MicroRNA for circulating tumor cells detection in breast cancer: In silico and in vitro analysis," 2009 ASCO Annual Meeting Abstract No. e22027, J Clin Oncol 27, (2009) (suppl) which is incorporated herein by reference). An analyte can include secreted exosomes. For example, secreted exosomes are indicative of some tumors (see Koga et al., "Purification, Characterization and Biological Significance of Tumor-derived Exosomes" Anticancer Research 25: 3703-3708 (2005), which is incorporated herein by reference). For example, an analyte can be Maspin (see Luppi et al., "Sensitive Detection of Circulating Breast Cancer Cells by Reverse-Transcriptase Polymerase Chain Reaction of Maspin Gene" Annals of Oncology, 7: 619-624 (1996), which is incorporated herein by reference). For example, analytes can include mammaglobin and B305D-C (see Reinholz et al., "Evaluation of a Panel of Tumor Markers for Molecular Detection of Circulating Cancer Cells in Women with Suspected Breast Cancer," Clinical Cancer Research 11: 3722-3732 (2005), which is incorporated herein by reference). See: U.S. Pat. No. 5,668,267 to Watson and Fleming, "Polynucleotides Encoding Mammaglobin, a Mammary-specific Breast Cancer Protein;" U.S. Pat. Nos. 5,855,889 and 5,968,754 to Watson and Fleming "Mammaglobin, a Mammary-specific Breast Cancer Protein;" U.S. Pat. No. 5,922,836 to Watson and Fleming "Mammaglobin Antigens;" U.S. Pat. No. 6,004,756 to Watson and Fleming "Method for Detecting the Presence of Breast Cancer by Detecting an Increase in Mammaglobin mRNA Expression;" and U.S. Pat. Nos. 6,566,072 and 6,677,428 to Watson and Fleming "Mammaglobin, a Secreted Mammary-specific Breast Cancer Protein;" which are each incorporated herein by reference.

The term "analytes," as used herein, also includes analytes that are indicators, or markers, for tissue characteristics associated with tissue changes and neoplasia, such as: excessive cellular growth; inflammation; oxygen use; vascularization;

and necrosis. For example, it has been demonstrated that hypoxic regions of breast cancer masses excrete the analyte lactate (see Semenza, "Tumor Metabolism: Cancer Cells Give and Take Lactate," Journal of Clinical Investigation, 118(12): 3835-3837 (2008), which is incorporated herein by reference). Other markers for hypoxia in solid tumors have been found (see Favaro et al., "Gene Expression and Hypoxia in Breast Cancer," Genome Medicine, 3(55) (2011), which is incorporated herein by reference). For example, multiple markers, including VPF/VEGF, flt-1, KDR, thrombospondin-1, collagen type I, fibronectin, versican and decorin, indicate the generation of vascular stroma in invasive breast carcinoma, breast carcinoma in situ and metastatic breast carcinoma (see Brown et al., "Vascular Stroma Formation in Carcinoma in Situ, Invasive Carcinoma, and Metastatic Carcinoma of the Breast," Clinical Cancer Research 5: 1041-1056, (1999), which is incorporated herein by reference). For example, analytes can include human epidermal growth factor receptor (hEGFR: see Li et al., "Inhibition of Cell Proliferation by an Anti-EGFR Aptamer," PLoS One, 6(6): e20299 (2011), which is incorporated herein by reference). For example, analytes can include markers of a reactive tumor stroma (see Radisky and Radisky, "Stromal Induction of Breast Cancer: Inflammation and Invasion," Rev Endocr Metab Disord. 8: 279-287 (2007), which is incorporated herein by reference). In some embodiments, analytes include biochemical markers for inflammation, which can indicate a physiological reaction to the implant itself or a change in the tissue independent of the implant.

Information from the plurality of sensor modules 150 A, B, C, D, E, F and G integrated with the breast implant 140 described herein can assist in monitoring of breast tissue health and potential changes in breast tissue over time. By virtue of its capability of analytes in fluid proximate to the breast implant 140, devices and systems described herein can monitor a significant portion of the total breast tissue over time from the interior of the breast for cellular changes, such as the development of neoplasia and cancer. The plurality of sensor modules 150 A, B, C, D, E, F and G integrated with the breast implant 140 can detect analytes present in interstitial fluid. The plurality of sensor modules 150 A, B, C, D, E, F and G integrated with the breast implant 140 can be configured to detect analytes present in interstitial fluid proximal to the breast implant 140. For example, information from the plurality of sensor modules 150 A, B, C, D, E, F and G integrated with the breast implant 140 described herein can assist in monitoring for breast cancer, hyperplasia, and related changes in breast tissue. For example, information from the plurality of sensor modules 150 A, B, C, D, E, F and G integrated with the breast implant 140 described herein can assist in monitoring for cell changes within the tissue. Information from the plurality of sensor modules 150 A, B, C, D, E, F and G integrated with a breast implant 140 as described herein can be used by an individual and the individual's medical team to inform decisions regarding further screening, such as mammography, magnetic resonance imaging (MRI) exams, and needle biopsies. Some embodiments of the breast implants described herein are configured to be compatible for further screening modalities. For example, some embodiments of the breast implants described herein are configured to include minimal ferromagnetic material. For example, some embodiments of the breast implants described herein are configured to be radiolucent. For example, some embodiments of the breast implants described herein include internal shielding. Information from the plurality of sensor modules 150 A, B, C, D, E, F and G integrated with the breast implant 140 described herein can be used by an individual and the individual's medical team to decide if further screening is warranted, or if such additional screening is not indicated at a particular time. In an embodiment, each of the plurality of sensor modules (e.g., sensor modules 150 A, B, C, D, E, F and G as shown in FIG. 1) has its own unique identifier, information can be specified as arising from that specific module and, therefore, being relevant to the adjacent tissue. This information informs as to the appropriate region of the breast tissue that can warrant further screening.

It is envisioned that the sensor modules utilized in the embodiments described herein can functionally persist in vivo for a period of years. Although a direct estimate of the duration of the functionality of a specific sensor module depends on the specific embodiment, some embodiments envisioned herein are estimated to provide information regarding analytes for a period of no less than 5 years after the implantation surgery, while some are envisioned to provide information regarding analytes in breast tissue for approximately 5 to approximately 10 years after implantation and initiation of use. For example, embodiments including a number of sensor units that are uncovered or activated over time can provide analyte detection over an extended period of time. For example, some of the sensor units described herein are estimated to provide functional analyte detection for a period of years. For example, some of the sensor units described herein may be recharged or refreshed. In some situations, a particular patient using a breast implant such as those described herein may choose to not have her breast implant replaced when it ceases to function to monitor analytes from adjacent breast tissue. The implant structure itself will persist and continue to provide aesthetic benefits even without operational sensor modules. The used or depleted sensor modules will be inert, and not require removal. For example, a woman undergoing breast reconstruction after mastectomy may be most interested in analyte detection in the first five years after the initial cancer diagnosis, as such detection may indicate a relapse, or the persistence of cancer that was not adequately removed at the initial surgery. An implant such as described herein may be desirable to monitor the five year post-cancer diagnosis interval in a cancer patient after reconstruction. See The American Cancer Society., Breast Cancer Facts & Figures 2011-2012: Atlanta: American Cancer Society, Inc., which is incorporated herein by reference.

In some embodiments, breast implants can be configured to minimally interfere with further screening through other modalities. For example, a breast implant can be fabricated with no or minimal amounts of ferromagnetic materials, so as to not potentially interfere with later screening techniques that employ magnetic resonance, such as MRI screening. See, for example, US Patent Application Publication No. 2011/0077736 to Rofougaran, "Breast Implant System Including Bio-Medical Units," which is incorporated herein by reference. For example, a breast implant can be configured to form minimal shadowing in mammography, such as being fabricated with materials that do not reflect or refract X-rays. For example, a breast implant can be configured for compatibility with ultrasound screening, such as being fabricated with materials that do not reflect or refract ultrasound waves. In some embodiments, breast implants include shielding for one or more features. For example, a breast implant may include shielding of a power source. For example, a breast implant may include shielding of a wire connector. A breast implant 140 can include shielding to minimize disruption of the breast implant by other screening modalities. See, for example, US Patent Application Publication No. 2007/0106332, "MRI Compatible Implanted Electronic Medical Device," to Denker et al., which is incorporated herein by reference.

Breast implants configured to detect different analytes will be of interest to different patients, for example women who have previously had a breast cancer diagnosis (e.g. reconstructive surgery patients) in comparison with women who have not had a breast cancer diagnosis (e.g. augmentation surgery patients). A woman who has had a previous history of breast cancer can choose a breast implant with sensor modules configured to detect the type of cancer that she had previously, e.g. to monitor for a reoccurrence. In contrast, a woman who has been never diagnosed with breast cancer can choose a breast implant with sensor modules that are configured to detect cellular changes indicative of breast cancer more generally, or other tissue changes that may have medical consequences. For example, a woman who has been previously diagnosed with HER-2/Neu positive breast cancer may be concerned with a recurrence of the original cancer after mastectomy (i.e. regrowth of the tumor from a small number of tumor cells not removed at surgery) and, therefore, may choose a breast implant including sensor modules configured to respond to excessive levels of the Her-2/Neu protein. For example, a woman who has previously been diagnosed with estrogen receptor-positive breast cancer (ER+) may be concerned with recurrence of the original tumor after lumpectomy and therefore, can choose a breast implant including sensor modules configured to respond to the presence of ER+ cells. For example, sensor modules in a breast implant can be configured to respond to the presence of abnormally high levels of estrogen receptor, such as found in some cancer tissues. For example, a woman without a history of breast cancer diagnosis can choose a breast implant for use in augmentation surgery that is configured to detect indicators of breast cancer generally, such as mammoglobin, maspin, or matrix metaloproteinases. For example, a woman without a history of breast cancer diagnosis can choose a breast implant for use in augmentation surgery that is configured to detect indicators of tissue inflammation in the breast. For example, a woman without a history of breast cancer diagnosis can choose a breast implant for use in augmentation surgery that is configured to detect indicators of neoplastic growth, such as vascularization, hypoxia, increased cellular division, and necrosis. See also: American Cancer Society., Breast Cancer Facts & Figures 2011-2012: Atlanta: American Cancer Society, Inc., which is incorporated herein by reference.

The analytes detected by the sensor modules are present in the fluid in the tissue adjacent to the breast implant, which can include interstitial or extracellular fluid, lymph, and blood. This fluid passes through the fluid-permeable cover to a region adjacent to the sensor modules during use. Multiple studies have indicated that cells, including cancer cells, release cellular components into the interstitial or extracellular fluid in tissue, and that such cellular components are indicative of the originating cell type. Proteins secreted from tumor cells, or a portion of the "secretome," can serve as markers for the presence of tumor cells. See, for example: Kulasingham and Diamandis, "Tissue Culture-based Breast Cancer Biomarker Discovery Platform," International Journal of Cancer 123: 2007-2012 (2008); and Wiig et al., "Interstitial Fluid: the Overlooked Component of the Tumor Microenvironment?" Fibrogenesis & Tissue Repair 3:12 (2010), which are each incorporated herein by reference. Surface proteins shed from cells can also serve as markers for the presence of tumor cells. In some embodiments, whole or partial cancer cells, such as metastatic cells, can be detectable via their specific surface proteins.

Referring again to FIG. 1, the breast implant 140 includes a shell 145, which is substantially filled with a viscous material configured to impart shape and texture to the breast 100. Some embodiments include low profile implants. The viscous material is compatible with biological implants. For example, the shell 145 can be substantially filled with a saline solution. For example, the shell 145 can be a silicone-based barrier layer substantially filled with silicone gel. For example, the breast implant 140 can include a shell 145 fabricated from a single gel barrier layer configured to surround an elastomeric gel, as described in U.S. Pat. No. 8,043,373 "All-Barrier Elastomeric Gel-Filled Breast Prosthesis," to Schuessler and Powell, which is incorporated herein by reference. For example, the breast implant 140 can include a shell 145 configured to include a variable cohesive gel, such as described in U.S. Pat. No. 8,070,808 "Variable Cohesive Gel Form-Stable Breast Implant" to Maxwell et al., which is incorporated herein by reference. For example, the breast implant 140 can include a shell 145 that includes internal partitions configured to be surrounded by a fluid gel, such as described in U.S. Pat. No. 3,559,214 "Compound Prosthesis" to Pangman, which is incorporated herein by reference. The breast implant 140 can include other internal features, such as reservoirs, ports, expandable regions, sealing regions and stabilizing features. See, for example US Patent Application No. 2011/0208302 "Reconstructive Breast Prosthesis" to Glicksman, which is incorporated herein by reference. The breast implant 140 can include a minimally invasive profile during implantation surgery, such as described in International PCT Publication No. WO 2008/014283 to Burnett, "Method and Apparatus for Minimally Invasive Implants" which is incorporated herein by reference.

The shell 145 of the breast implant 140 can include a single layer, such as of elastomeric polymer or firm silicone. The shell 145 of the breast implant 140 can be fabricated from a bio-compatible material. The shell 145 is configured to maintain the structural integrity of the implant without rupture or leakage of the viscous material inside the shell 145. In some embodiments, a breast implant 140 includes a shell 145 that includes at least two barrier layers. For example, a breast implant 140 can include a shell 145 made up of two or more layers of silicone. For example, a breast implant 140 can include a shell 145 fabricated from two or more sheets of elastomeric polymer. A shell 145 of a breast implant 140 can include a plurality of barrier layers, or layers of material configured to maintain the structural integrity of the implant without rupture or leakage. The breast implant 140 can include a shell with electrically insulating properties surrounding a low-conductance filler material, such as described in International PCT Publication No. WO 2008/014283 to Burnett, "Method and Apparatus for Minimally Invasive Implants" which is incorporated herein by reference. The breast implant 140 can include a shell with properties that inhibit tumor cell growth. See, for example, Zhang and Webster, "Poly-lactic-glycolic-acid surface nanotopographies selectively decrease breast adenocarcinoma cell functions," Nanotechnology 23: 155101 (2012), which is incorporated herein by reference.

The breast implant 140 includes at least one fluid-permeable cover 155 completely enveloping the shell 145. For example, as illustrated in FIG. 1, a cover 155 surrounds the shell 145 with a gap 160 between the cover 155 and the shell 145. In some embodiments, a cover 155 is configured to completely envelop the shell 145 with a uniform gap 160 between the cover 155 and the shell 145. In some embodiments, a cover 155 has an internal diameter that is larger than the largest exterior diameter of the shell 145. As shown in FIG. 1, in some embodiments a cover 155 is approximately the same shape as the shell 145 to maintain a uniform gap 160 between the shell 145 and the cover 155. A plurality of projections 165 form a series of compartments in the gap 160 between the shell 145 and the cover 155. Each projection extends from an outer surface of the shell 145 to an inner surface of the cover 155. During use, interstitial fluid from the tissue adjacent to the breast implant 140 (e.g. as identified as 112, 110, 114, 124, 120 and 122 in FIG. 1) will move into the compartments of the gap 160 adjacent to the sensor modules 150 A, B, C, D, E, F and G oriented around the exterior of the breast implant 140 (illustrated with the dotted arrows in FIG. 1). The cover 155 can be configured to filter excess cellular material from the breast implant 140, including the sensor modules 150, and therefore prevent clogging or fouling of the sensor modules 150. The cover 155 can be configured to prevent lymphocytes and other immune response cells from interacting with the surface of the shell 145 and the sensor modules 150, thereby minimizing immune response to the breast implant 140 over time. The cover 155 can be configured to encourage normal cellular growth in the tissue adjacent to the breast implant 140, thereby increasing fluid flow through the region and minimizing the formation of scar tissue. The breast implant 140 can include a cover 155 fabricated from an analyte-permeable material. For example, the cover 155 may include pores or openings of sufficient size and shape to allow analytes detectable by the sensor modules 150 to flow through the cover 155. In a particular embodiment, the cover 155 can be permeable to one or more type of analytes corresponding to types of analytes detected by the sensor modules 150 and largely impermeable to other analytes. For example, the cover 155 can include pores or holes of a size and shape to exclude material present in interstitial fluid that is larger than the analyte(s) detected by the sensor modules 150 attached to the shell 145. For example, the cover 155 can include pores or holes of a size and shape to exclude whole lymphocyte or epithelial cells, while permitting the movement of proteins, nucleic acids, polysaccharides, and other cellular components through the cover 155. The breast implant 140 can include a cover 155 fabricated from an analyte-permeable material that promotes the movement of a specific analyte or type of analytes through the cover 155. For example, the cover 155 can include a surface charge that attracts types of analytes corresponding to analytes detected by the sensor modules 150 in a particular embodiment, and repelling other types of analytes. The breast implant 140 can include a cover 155 fabricated from a variety of materials, depending on the embodiment. For example, the breast implant 140 can include a cover 155 fabricated from a plastic material, or from a fabric material. For example, the cover 155 can include polytetrafluoroethylene (PTFE) (e.g. Teflon™ or Gore-tex™ materials). For example, the breast implant 140 can include a cover 155 fabricated from a bio-compatible material. The breast implant 140 can include a cover 155 fabricated from a mesh structure. The breast implant 140 can include a cover 155 fabricated from a porous structure. For example, a cover 155 with a porous structure can include pores that are configured to form a biocompatible layer between the cover 155 and the adjacent tissue. See, for example, US Patent Application No. 2011/0282444 to Liu et al., "Porous Materials, Methods of Making and Uses" which is incorporated herein by reference. The breast implant 140 can include a cover 155 with a fluid control film component oriented to permit directional flow of interstitial fluid into and out of the gap 160. See, for example, U.S. Pat. No. 6,420,622 to Johnston et al., "Medical Article Having Fluid Control Film," which is incorporated herein by reference. The breast implant 140 can include a cover 155 with properties that inhibit tumor cell growth. See, for example, Zhang and Webster, "Poly-lactic-glycolic-acid surface nanotopographies selectively decrease breast adenocarcinoma cell functions," Nanotechnology 23: 155101 (2012), which is incorporated herein by reference. The breast implant 140 can include a cover 155 with a three dimensional conformation or architectural structure at the host interface that promotes close vascularization from the tissue immediately surrounding the implant 140 (e.g. as identified as 112, 110, 114, 124, 120 and 122 in FIG. 1), thereby increasing the adjacent fluid available for sampling. See, for example, U.S. Pat. No. 5,800,529 to Brauker et al., "Close Vascularization Implant Material," which is incorporated herein by reference. A cover 155 can include a biointerface membrane configured to improve the biointerface between implantable devices and the adjacent tissue. See, for example, U.S. Pat. No. 7,364,592 to Carr-Brendel et al., "Biointerface Membrane with Macro- and Micro-Architecture," which is incorporated herein by reference. A cover 155 can include an additional coating. See U.S. Pat. Nos. 6,119,028 and 6,477,395, "Implantable Enzyme-Based Monitoring Systems Having Improved Longevity Due to Improved Exterior Surfaces," to Schulman et al., which are each incorporated herein by reference. A cover 155 can be fabricated from materials expected to provide a natural feel to the breast implant 140, for example silicone or soft polymer. A cover can be configured to provide texture or cushioning to a breast implant 140 to improve the aesthetics of the breast implant 140.

A plurality of projections 165 extend from an external surface of the shell 145, the projections 165 forming a plurality of compartments adjacent to the external surface of the shell 145. The projections 165 can be configured as partitions. The plurality of projections 165 can be configured as a plurality of membranes attached to the external surface of the shell 145. For example, the plurality of projections 165 can be configured as a plurality of membranes attached to the external surface of the shell 145 with a fluid-resistant seal at the junction between the external surface of the shell 145 with the plurality of projections 165. The projections 165 can include a first end surface sealed to the external surface of the shell, and a second end surface sealed to a surface of the cover. The projections 165 form a series of compartments adjacent to the surface of the shell 145, for example around the sensor modules 150 on the surface of the shell 145. Some embodiments include one sensor module 150 in each compartment. Some embodiments include a plurality of sensor modules 150 in each compartment. The compartments can include a region of the cover forming a side of each of the compartments, the region including at least one set of influx microchannels configured to direct fluid into the compartment, and including at least one set of efflux microchannels configured to direct fluid out of the compartment. The compartments can be substantially sealed from each other. For example, each of the compartments can be impenetrable to direct transfer of fluid from compartment to compartment. The compartments can be oriented with an approximate axis from the top of the breast implant to the bottom, with direction as expected during in vivo use. For example, the compartments can be oriented with an approximate axis from the top of the breast implant to the bottom, so that gravity can be expected to assist in fluid flow from the top to the bottom through each compartment during in-vivo use. The compartments can be substantially sealed from each other. For example, the compartments can be positioned and configured to minimize fluid flow directly between the compartments.

FIG. 1 also illustrates that the breast implant 140 includes a plurality of sensor modules 150 A, B, C, D, E, F and G oriented around the exterior of the breast implant 140. It will be appreciated that even though FIG. 1 depicts seven sensor modules, any number of sensor modules can be used. The sensor modules 150 A, B, C, D, E, F and G are oriented to detect one or more analytes in a fluid between the shell 145 and the cover 155, the fluid arising from tissue adjacent to the breast implant 140, such as in interstitial fluid from the surrounding tissue. The sensor modules 150 A, B, C, D, E, F and G are positioned at a distance from each other around the exterior surface of the shell 145. The sensor modules 150 A, B, C, D, E, F and G can be positioned in a substantially equidistant orientation around the surface of the shell 145. As discussed further below, some of the sensor modules 150 A, B, C, D, E, F and G can be clustered around the surface of the shell 145 to more fully monitor a region or area of adjacent breast tissue. In some embodiments, the sensor modules can be positioned in an irregular orientation, for example to more comprehensively monitor a specific adjacent region of tissue, such as a previous cancer site or another region of interest. The sensor modules 150 A, B, C, D, E, F and G can be oriented to function as an array, a web or as part of a nodal network. The sensor modules 150 A, B, C, D, E, F and G are oriented and positioned to monitor analytes in fluid from the breast tissue surrounding the breast implant 140. The sensor modules 150 A, B, C, D, E, F and G can be configured to detect one or more biological analytes arising from biological tissue, such as the breast tissue adjacent to a specific sensor module. The sensor modules 150 A, B, C, D, E, F and G can be oriented and positioned to monitor analytes in fluid from a comprehensive sampling of the breast tissue surrounding the breast implant 140. The region of breast tissue monitored and the sensitivity of the monitoring depends on factors including the type of sensor modules, the position of the sensor modules, the orientation of the sensor modules, and the density of the sensor modules. The sensor modules 150 A, B, C, D, E, F and G shown in FIG. 1 are positioned and oriented to detect analytes in interstitial fluid substantially around the entire periphery of the breast implant 140.

Devices and systems described herein can monitor a significant percentage of the tissue within the total interior of a breast over time for cellular changes, such as the development of cancer, by detecting analytes in interstitial fluid around the entire periphery of the breast implant 140. In some embodiments, the sensor modules are positioned to enhance monitoring of tissue in one or more regions of particular interest. Although the size and positioning of particular breast implants will vary depending on the specific individual patient and breast tissue morphology, a breast implant 140 includes a shell 145 and a cover 155 with an external surface that is positioned within and adjacent to breast tissue.

Different breast implants will be fashioned in different sizes and shapes, and sensor modules can be of any range of sizes. The positioning and total number of sensor modules attached to a breast implant will vary depending on the embodiment. As breast implant sizes depend on the specific embodiment, the corresponding space available for the placement of sensor modules depends on the specific implant. The breast implant 140 illustrated in FIG. 1 is depicted as an elongated teardrop shape with a flattened back region, but in some embodiments a breast implant 140 will be configured as an ellipse, an ovoid, a disk or other shape. Therefore, depending on the shape and size of the breast implant 140 utilized in a given embodiment, the potential positions and numbers of sensor modules 150 will vary. However, for a breast implant 140 of any given shape and size, the number and position of sensor modules 150 around the circumference of the shell 145 will be selected to provide sampling of fluid adjacent to the periphery of the cover 155.

In some embodiments, sensors may be clustered or oriented to provide additional monitor capability in regions of breast tissue of particular interest. For example, a region of a breast implant 140 adjacent to the original tumor locus can have additional sensor modules 150 for use in reconstructive surgery. For example, a region of the breast implant 140 that may be adjacent to a breast tissue region difficult to visualize through mammography, such as a region of the implant 140 positioned adjacent to the chest wall (e.g. regions 122, 120 and 124 in FIG. 1) can have additional sensor modules 150 to provide additional monitoring capability in that tissue region.

Figure 2:
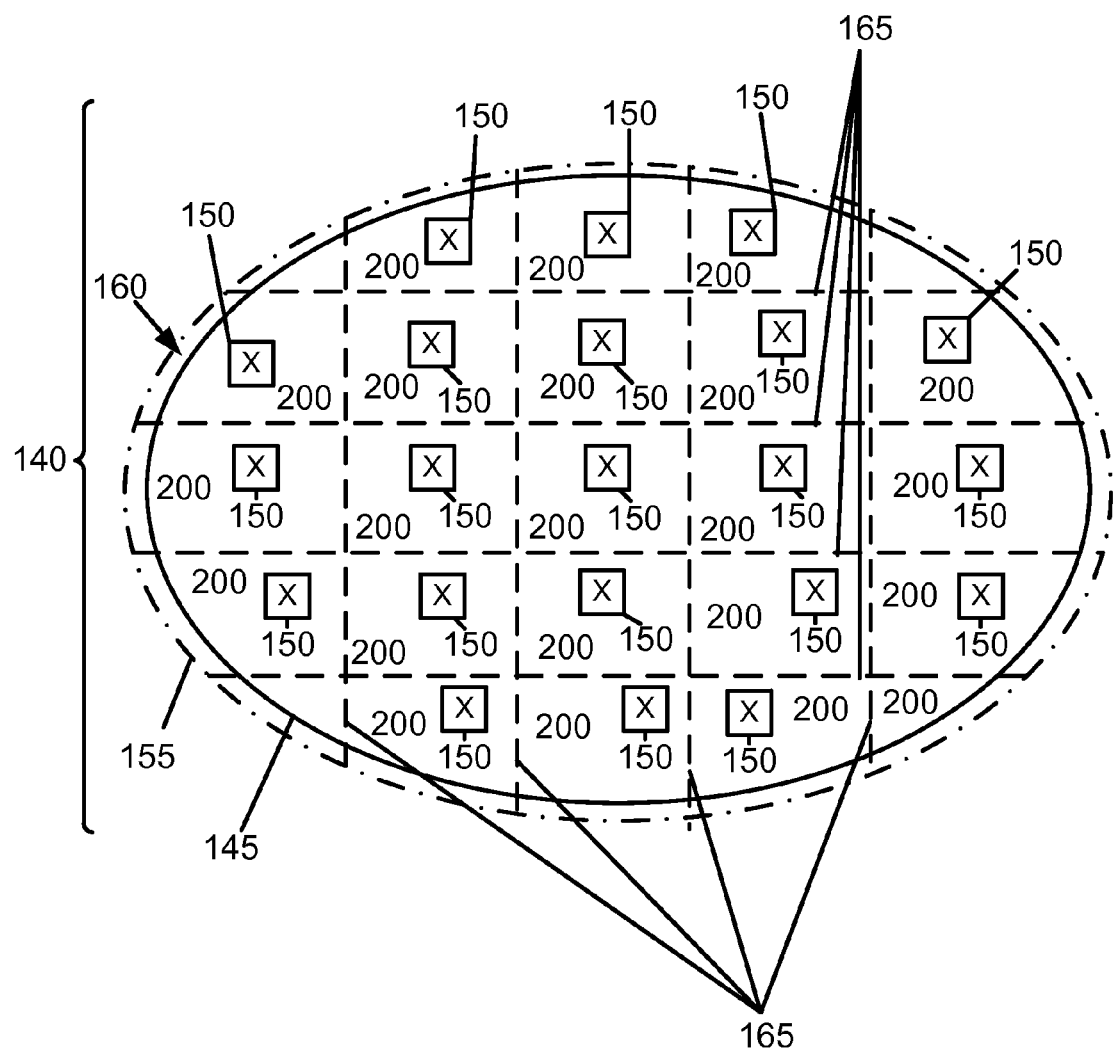
FIG. 2 is a schematic of a breast implant ex vivo from an external view.

In some embodiments, such as illustrated in FIGS. 1 and 2, sensor modules 150 of a single type are attached to and approximately equally distributed around the external surface of the shell 145 of the breast implant 140. However, in some embodiments, regions of unequal density and/or sensor module types may be fabricated and implemented. In some embodiments, sensor modules 150 are positioned on a breast implant 140 in a region of interest for monitoring. For example, in an embodiment wherein the region adjacent to the chest wall is of particular interest in monitoring for cellular changes, the region of the shell 145 of the breast implant 140 configured to be positioned adjacent to the chest wall may have a higher density of sensor modules 150 attached than other regions of the breast implant 140.

In some embodiments, sensor modules 150 of particular types may be attached to particular regions of the shell 145 of the breast implant 140. For example, sensor modules 150 configured to detect changes in ductal breast tissue may be attached to the region of the shell 145 of the implant 140 adjacent to most of the ductal tissue (e.g. a front-facing portion of the implant 140) in a particular individual. For example, sensor modules 150 configured to detect changes in breast tissue in the regions of the chest wall may be attached to the region of the shell 145 of the implant 140 adjacent to the chest wall (e.g. a rear-facing portion of the implant 140) in a particular individual. In some embodiments, some regions of the shell 145 of the breast implant 140 are left with few or none sensor modules 150 and other regions include a dense coverage of sensor modules 150.

In some embodiments and as illustrated in FIG. 1, each of the sensor modules 150 includes a unique identifier for that sensor module 150. For example, FIG. 1 includes sensor modules 150 A, B, C, D, E, F and G, wherein each of the letter designations represents a unique identifier for that sensor module 150. A unique identifier for a sensor module 150 is a specific identifier that denotes that sensor module 150 (e.g. 150 A) and no other sensor module 150 (e.g. 150 B, C, D, E, F and G). As an additional example, FIGS. 3, 4, 5 and 6 include sensor modules 150 A, B, C, and D, wherein each of the letter designations represents a unique identifier for that sensor module 150. In some embodiments, a unique identifier associated with a sensor module includes an alphanumeric code. An alphanumeric code is made up of some combination of letters and numbers, such as 123, ABC, 12B34, AB34CD, or similar codes. In some embodiments, a unique identifier for a sensor module includes a positional identifier. A positional identifier includes information relative to the specific size and shape of a particular breast implant 140. For example, a positional identifier for a sensor module may include positional information such as "upper right front corner" or "lower center of rear face" or similar information. For example, a positional identifier for a sensor module may include positional information such as "grid location 1A" or "intersection of gridlines X and Y." For example, a positional identifier for a sensor module may include positional information such as "within compartment number 12." In some embodiments, a unique identifier for a sensor module includes an electronic code, such as a radio frequency identification (RFID) identifier code. In some embodiments, a unique identifier for a sensor module includes a digital code. In some embodiments, a unique identifier for a sensor module includes an analog code. In some embodiments, a unique identifier for a sensor module includes a machine code. In some embodiments, sensor modules of a particular type can have a common identifier; wherein such identifier is different from those of sensor modules of a different type.

FIG. 2 illustrates further aspects of a breast implant 140 with a plurality of attached sensor modules 150. Illustrated in FIG. 2 is an external, ex-vivo view of a breast implant 140. FIG. 2 illustrates an embodiment wherein the plurality of sensor modules 150 attached to the shell 145 of the breast implant 140 are substantially equally positioned over the surface of the shell. A cover 155 completely surrounds and envelops the shell 145. A gap 160 is located between the cover 155 and the shell 145. A series of projections 165 are arranged in a grid-like array over the surface of the shell 145. In the view shown in FIG. 2, the projections are configured as flat sheets surrounding the circumference of the shell 145 and positioned at approximate right angles to the shell 145. FIG. 2 illustrates the projections 165 as partitions between the plurality of compartments 200. In the view shown in FIG. 2, the projections form a plurality of compartments 200, each of the compartments 200 including a sensor module 150. The plurality of sensor modules 150 attached to the shell 145 of the breast implant 140 shown in FIG. 2 are attached in an approximately even distribution on the shell 145 surface. The plurality of sensor modules 150 attached to the shell 145 of the breast implant 140 shown in FIG. 2 are attached in a grid-like array. The flat view illustrated in FIG. 2 is a depiction of a plurality of sensor modules 150 attached to the shell 145 of the breast implant 140 and does not fully represent the 3-dimensional nature of the distribution of the sensor modules 150 and the compartments 200 on a shell 145 that is substantially curved or includes an arc structure.

A breast implant 140 can include a grid over the surface of the shell 145 of the breast implant 140. A grid can be visible, invisible to a standard observer, or virtual. Position-indicating lines can serve to describe regions of the surface of the shell 145 of a breast implant 140. For example, intersecting lines can indicate the location on the surface of the shell 145 corresponding to the location of a particular sensor module. The location of the particular sensor module can be identified as the "intersection of line X and line Y." Similarly, regions of a shell 145 surface including more than one sensor module 150 can be identified by the positional lines surrounding that region of the shell 145 surface. Some embodiments can include grid lines in an irregular or uneven pattern, for example to correspond to the surface shape of a breast implant 140 of an irregular or uneven shape. Some embodiments can include other positional marks, such as edge identifiers, quadrant positional marks, or similar identifiers of position on the surface of the shell 145. Some embodiments can include positional marks that are not visible, such as virtual marks based on physical features of the breast implant 140, such as "a location 3 cm from the upper right quadrant" or similar positional information. Some embodiments can include fiducial markers.

Figure 3:
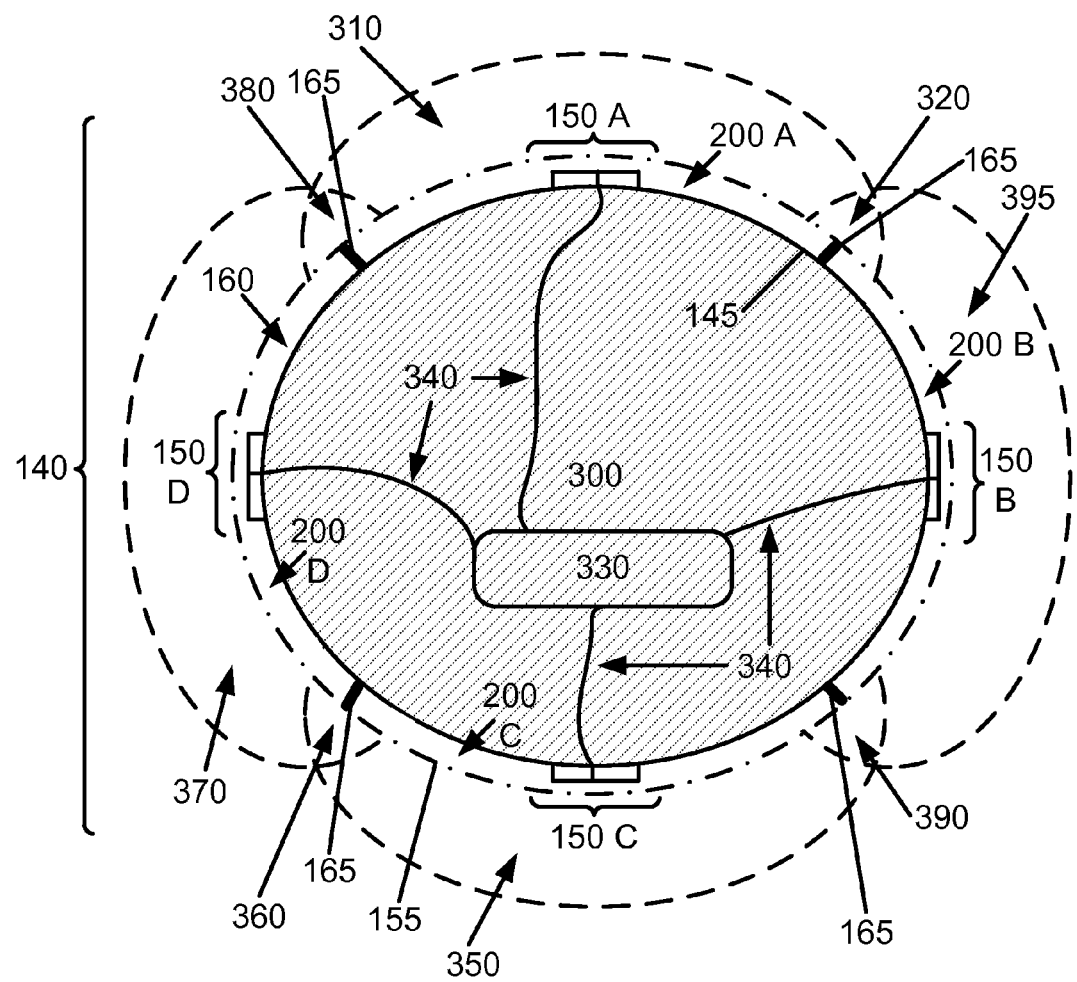
FIG. 3 is a schematic of a breast implant ex vivo in cross-section view.

Further aspects of a breast implant 140 are illustrated in FIG. 3. FIG. 3 shows a cross-sectional view of a breast implant 140 ex-vivo. FIG. 3 illustrates a breast implant 140 with an outer shell 145 and an interior 300 substantially filled with a viscous material. A cover 155 completely surrounds and envelops the shell 145 with a gap 160 between the shell 145 surface and the cover 155 surface. A plurality of projections 165 extend from an external surface of the shell 145, the projections 165 forming a plurality of compartments 200 A, B, C, D adjacent to the external surface of the shell 145. In the view shown in FIG. 3, sensor modules 150 A, 150 B, 150 C and 150 D are distributed approximately equally around the external surface of the shell 145. FIG. 3 illustrates an embodiment wherein the breast implant 140 has been cut approximately in half along a plane corresponding to the widest part of the breast implant 140. In general, the implant 140 is of a size and shape desirable in a particular embodiment and the sensor modules 150 A, B, C and D are correspondingly positioned relative to each other. For example, a breast implant 140 that is approximately 12.5 cm across (e.g. in a straight line between sensor modules 150 D and 150 B) and approximately 12 cm long (e.g. in a straight line between sensor modules 150 A and 150 C), the total perimeter of the shell 145 would be approximately 76 cm and the distance between the center of each sensor module 150 (e.g. 150 A) and its adjacent sensor modules 150 (e.g. 150 D and 150 B) would be approximately 19 cm along the surface of the shell 145. For example, embodiments can include breast implants including a plurality of sensor modules attached to the shell, and wherein the centers of the sensor modules attached to the shell are separated by distances of approximately 5 to approximately 8 cm. For example, embodiments can include breast implants including a plurality of sensor modules attached to the shell, and wherein the centers of the sensor modules attached to the shell are separated by distances of approximately 3 to approximately 6 cm. For example, embodiments can include breast implants including a plurality of sensor modules attached to the shell, and wherein the centers of the sensor modules attached to the shell are separated by distances of approximately 1 to approximately 4 cm. For example, embodiments can include breast implants including a plurality of sensor modules attached to the shell, and wherein the centers of the sensor modules attached to the shell are separated by distances of less than approximately 1 cm. Some embodiments that include sensor modules fabricated on a microsensor scale or a nanosensor scale, with corresponding small distances between the sensor modules.

As shown in FIG. 3, a power source 330 is located within the interior 300 of the shell 145 of the breast implant 140. The power source 330 illustrated in FIG. 3 is operably attached to the plurality of sensor modules 150 A, 150 B, 150 C and 150 D through the wire connections 340. The power source 330 illustrated in FIG. 3 is positioned substantially within the shell 145. As shown in FIG. 3, the power source 330 is not directly attached to the shell 145. However, the reader will appreciate that the power source can be located exterior to the shell 145 of the implant. Although not illustrated in FIG. 3, there may be additional tethers, supports or internal structures within the breast implant 140 attached to the power source 330 and stabilizing the relative position of the power source 330. For example, the breast implant 140 can include a shell 145 that includes a power source attached to internal partitions, such as those described in U.S. Pat. No. 3,559,214 "Compound Prosthesis" to Pangman, which is incorporated herein by reference. For example, the breast implant 140 can include a shell 145 that includes a power source attached to stabilizing features such as those described in US Patent Application No. 2011/0208302 "Reconstructive Breast Prosthesis" to Glicksman, which is incorporated herein by reference. In some embodiments, a power source 330 can be attached to an exterior surface of the shell 145. In some embodiments, a power source 330 can be integrated into a sensor module 150 and attached as part of the sensor module 150 to the external surface of the shell 145. Although not illustrated in FIG. 3, in some embodiments each sensor module 150 can include its own power source 330. Although not illustrated in FIG. 3, in some embodiments there may be a plurality of power sources 330, and each power source 330 attached to a group of sensor modules 150.

A power source 330 can be of a variety of types, depending on the embodiment. A power source 330 can be an energy-storage device such as a battery, such as a thin film battery, a "button" battery, a rechargeable battery or a disposable battery. A power source 330 can be a battery configured for use with small implantable integrated circuits, such as described in European Patent Application No. 1,867,275 to Scarantino et al., "Systems Comprising Implantable Devices for Dynamic Monitoring of Tumors," which is incorporated herein by reference. A power source 330 can include the battery and capacitor power sources described in PCT International Application No. US2006/022761 to Mangrum et al., "Method and Apparatus for Monitoring Implants" which is incorporated herein by reference. A power source can include a thin film battery, such as described in U.S. Pat. No. 5,338,625 "Thin Film Battery and Method for Making Same," to Bates et al., which is incorporated herein by reference. A power source can include a battery fabricated on a micro-scale or a nano-scale. A power source can include a micro-battery or a nano-battery. A power source can be rechargeable. A power source can include a rechargeable battery.

A power source can include a wirelessly transmitted power source. See, for example: Laskovski et al., "Wireless Power Technology for Biomedical Implants," in Biomedical Engineering, DOI: 10.5772/7880; and Laskovski and Yuce, "Class-E Oscillators as Wireless Power Transmitters for Biomedical Implants," 3rd International Symposium on Applied Sciences in Biomedical and Communication Technologies ISABEL 2010 (2010), which are each incorporated herein by reference. A power source can include an implanted pulse generator. See, for example, US Patent Application Publication No. 2005/0143787 "Method and System for Providing Electrical Pulses for Neuromodulation of Vagus Nerve(s), Using Rechargable Implanted Pulse Generator," to Boveja and Widhany, which is incorporated herein by reference. A power source can include a piezoelectric power source that converts mechanical energy to electrical energy. A power source can include an ultrasound receiver and a transducer to convert the received ultrasound energy into power for the sensor module system. A power source can include a micro-generator. A power source can include a photovoltaic element that receives optical energy from an exterior source. A power source can include a micromechanical (MEMS) based power source. See, for example, Lueke and Moussa: MEMS-Based Power Generation Techniques for Implantable Bio-sensing Applications," Sensors, 11, 1433-1460; doi:10.3390/s110201433 (2011), which is incorporated herein by reference. A power source can include one or more biofuel cells. See, for example: Barton et al., "Enzymatic Biofuel Cells for Implantable and Microscale Devices," Chem. Rev. 104: 4867-4886 (2004); U.S. Pat. No. 3,941,135, "Pacemaker with Biofuel Cell" to von Sturm and Richter; U.S. Pat. No. 7,709,134, "Microfluidic Biofuel Cell," to Minteer et al.; US Patent Application Publication No. 2008/0160384, "Integrated Biofuel Cell with Aligned Nanotube Electrodes and Method of Use Thereof," to Iqbal and Wang; and US Patent Application Publication No. 2011/0250510, "Glucose Biofuel Cell," to Cinquin et al., which are each incorporated herein by reference. See U.S. Pat. No. 7,236,821, "Chronically-Implanted Device for Sensing and Therapy," to Cates, which is incorporated herein by reference.

FIG. 3 illustrates that each of the sensor modules 150 A, B, C, D are positioned and oriented on the shell 145 of the breast implant 140 so that each sensor module 150 A, B, C, D can monitor analytes in fluid from a specific region of breast tissue. Each of the sensor modules 150 A, B, C, D is positioned on the surface of the shell 145 at a distance from each other. Each of the sensor modules 150 A, B, C, D is oriented on the surface of the shell 145 to detect one or more analytes in a fluid within one of the plurality of compartments 200 A, B, C, D. As shown in FIG. 3, sensor module 150 A is positioned to monitor analytes in fluid in compartment 200 A, the fluid arising from tissue in the adjacent region identified as 310. FIG. 3 also illustrates that sensor module 150 B is oriented to monitor analytes in fluid in compartment 200 B, the fluid originating from tissue in the adjacent region identified as 395. FIG. 3 shows sensor module 150 C oriented to monitor analytes in fluid in compartment 200 C, the fluid originating from the adjacent tissue region indicated as 350. FIG. 3 also illustrates sensor module 150 D positioned to monitor analytes in fluid in compartment 200 D, the fluid arising from tissue in the adjacent region 370.

Since each of the sensor modules 150 A, B, C, D also can include its own unique identifier, any information regarding detected analytes in fluid while the breast implant 140 is in use is also informative for the corresponding adjacent region of tissue. For example, during in-vivo use an analyte in a fluid detected by sensor module 150 A can be expected to have arisen from adjacent tissue region 310. As an additional example, during in-vivo use a positive signal for an analyte arising from sensor module 150 B and including the specific identifier of sensor module 150 B can be assumed to come from an analyte flowing to the sensor module 150 B in fluid from tissue region 395. Also for example, if sensor module 150 C detects an analyte, that analyte can be expected to have arisen in the region of adjacent tissue identified as 350. As a further example, if information from sensor module 150 D indicates that an analyte has been detected, the analyte can be expected to have come from fluid in region 370. Identification of the region of tissue that an analyte is expected to have arisen from provides an individual and the individual's health care team information as to where a possible change in breast tissue has occurred, and therefore a region to focus further screening efforts. For example, a region of breast tissue with a positive indicator may be further screened through palpation or biopsy of the region. For example, a region of breast tissue with a positive indicator may be further screened through focused imaging such as ultrasound, MRI or mammography.

As illustrated in FIG. 3, the sensor modules 150 A, B, C, D may be positioned so that there is some overlap in the adjacent tissue that the sensor modules 150 A, B, C, D are reasonably expected to monitor fluid from during the expected use of the breast implant 140. Positioning the sensor modules 150 A, B, C, D in close enough proximity for overlapping regions of tissue to monitor fluid arising from them can reduce the chance that an analyte in tissue fluid adjacent to the breast implant 140 will fail to be detected by at least one of the sensor modules 150 A, B, C, D. Positioning the sensor modules 150 A, B, C, D with overlapping regions of sensitivity can also assist in locating the region of adjacent breast tissue that is a candidate for further screening. For example, if a system provides information that both sensor modules 150 A and 150 B have detected an analyte in fluid, the fluid can be expected to have been in the overlapping monitoring tissue region for both sensor modules A and B (illustrated in FIG. 3 as region 320). For example, if sensor modules 150 B and 150 C both detect an analyte in fluid from adjacent tissue, further screening can be focused on the tissue region that includes the sensitivity region of both sensor module 150 B and 150 C (e.g. region 390 in FIG. 3). As a further example, if both sensor modules 150 C and 150 D provide information that they have detected an analyte at a similar time, the analyte can have arisen in fluid from tissue region 360, and that region of breast tissue can be the focus of further screening. Also by way of example, if information arising from sensor modules 150 D and 150 A indicates that an analyte is present in the adjacent tissue of both sensor modules, an adjacent region such as indicated at 380 in FIG. 3 can be the subject of further screening.

Sensor modules can be attached to the surface of the shell using a variety of techniques. For example, in embodiments wherein the sensor modules are attached to an external surface of the 150 A, B, C, D, such as illustrated in FIG. 3, the sensor modules can be affixed to the surface using an adhesive. In some embodiments, one or more aspects of sensor modules are directly printed onto the surface of the shell.

Figure 4:
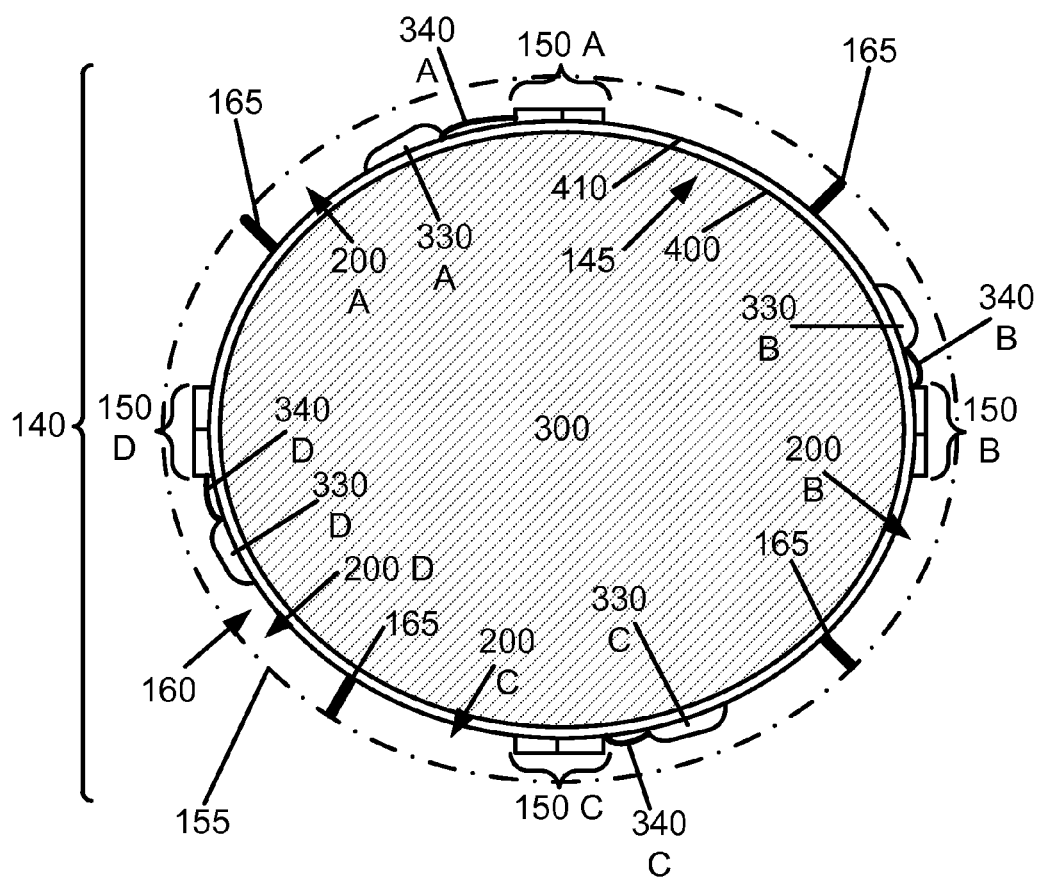
FIG. 4 is a schematic of a breast implant ex vivo in cross-section view.

FIG. 4 illustrates further aspects of a breast implant 140. The breast implant 140 depicted in FIG. 4 is shown in cross-section, a similar view as FIG. 3. However, the breast implant illustrated in FIG. 4 is a different embodiment than that illustrated in FIG. 3. FIG. 4 shows a breast implant 140 including a shell 145 substantially filled with a viscous material 300. A cover 155 completely surrounds and envelops the shell 145 with a gap 160 between the shell 145 surface and the cover 155 surface. A plurality of projections 165 extend from an external surface of the shell 145, the projections 165 forming a plurality of compartments 200 A, B, C, D adjacent to the external surface of the shell 145. The breast implant 140 illustrated in FIG. 4 includes sensor modules 150 A, B, C and D positioned at approximately equal distances from each other around the surface of the shell 145. Each compartment 200 A, B, C, D includes a sensor module 150 A, B, C, D. Each of the sensor modules 150 A, B, C, D is oriented to detect one or more analytes in a fluid within one of the plurality of compartments 200 A, B, C, D. As shown in FIG. 4, a breast implant 140 can include a plurality of power sources 330. The breast implant 140 includes a power source, 330 A, B, C, D attached to each of the sensor modules 150 A, B, C, D. Each of the power sources 330 A, B, C, D are attached to the exterior of the shell 145. Each of the power sources 330 A, B, C, D are attached to a sensor module 150 A, B, C, D with a wire connection 340 A, B, C, D. The wire connections 340 A, B, C, D are positioned adjacent to the exterior surface of the shell 145. Although not illustrated in FIGS. 3 and 4, there can be a plurality of power sources 330 connected to each sensor module 150. Similarly, each power source 330 can be connected to more than one sensor module 150.

FIG. 4 also illustrates a breast implant 140 wherein the shell 145 comprises a plurality of barrier layers. The different layers can provide, for example, additional protection against leakage of the interior viscous material 300 out of the breast implant 140 over a single barrier layer. The different layers can provide, for example, additional structure, such as for support for the sensor modules 150 A, B, C, D and the power sources 330 A, 330 B. The different layers can provide, for example, structure to stabilize the projections 165. The shell 145 illustrated in FIG. 4 includes two barrier layers 400, 410. The barrier layers 400 410 are substantially similar sizes and shapes, with the inner barrier layer 400 within and slightly smaller than the outer barrier layer 410. In FIG. 4, the barrier layers 400, 410 are in a nesting configuration relative to each other with a minimal volume of space between the layers 400, 410. In some embodiments, a plurality of barrier layers can be of different sizes, with a larger volume of space between the layers. The plurality of layers may be of different shapes with relative sizes to allow the layers to nest within each other. Structural features of the breast implant 140 may be positioned between barrier layers of the shell 145, and may be attached to one or more of the barrier layers. For example, one or more power sources 330 A, B, C, D may be positioned within the barrier layers 400, 410 of the shell 145 (e.g. between layer 400 and layer 410 as shown in FIG. 4). For example, one or more wire connections 340 A, B, C, D can be positioned within the barrier layers 400, 410 of the shell 145 (e.g. between layer 400 and layer 410 as shown in FIG. 4).

Figure 5:
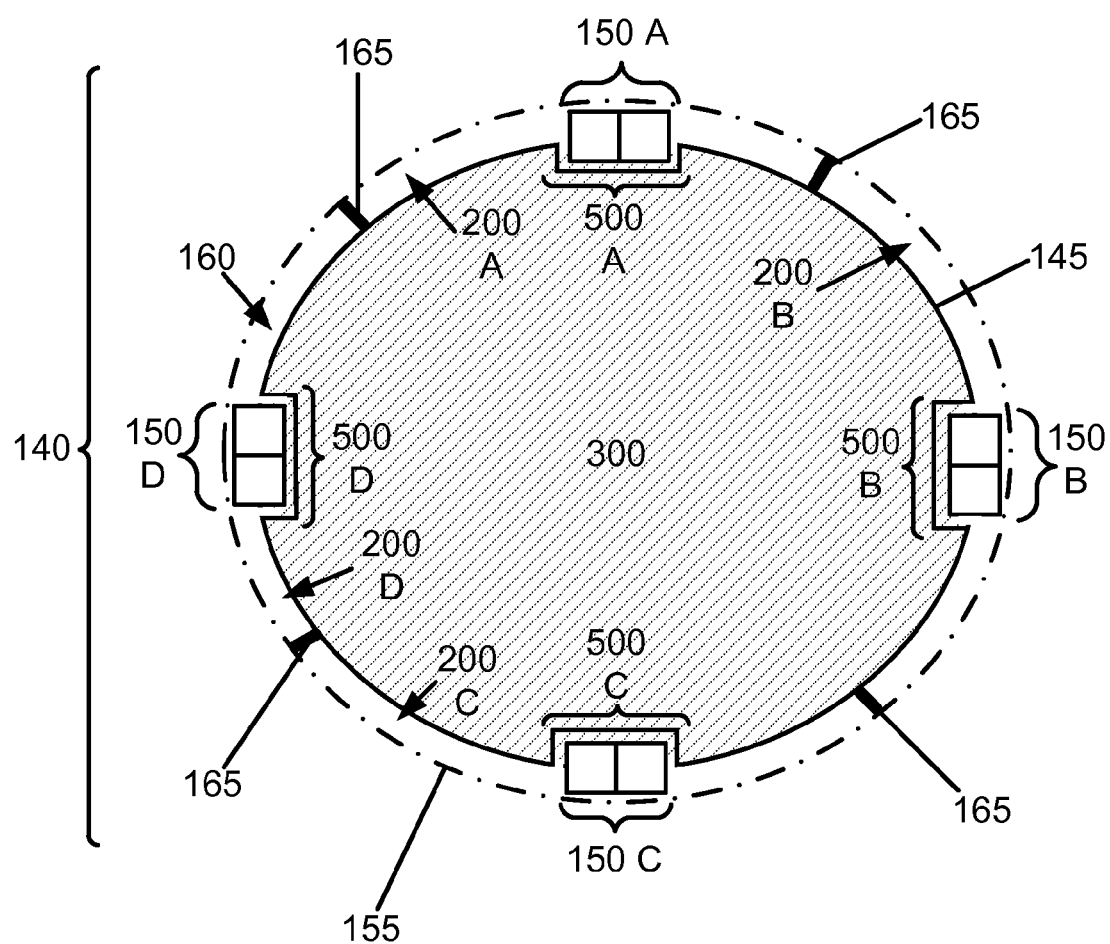
FIG. 5 is a schematic of a breast implant ex vivo in cross-section view.

FIG. 5 illustrates aspects of a breast implant 140 including a plurality of sensor modules 150 A, 150 B, 150 C and 150 D. The breast implant 140 depicted in FIG. 5 is shown in cross-section, a similar view as in FIGS. 3 and 4. The breast implant 140 includes interior viscous material 300. A cover 155 completely surrounds and envelops the shell 145 with a gap 160 between the shell 145 surface and the cover 155 surface. Projections 165 traverse the gap 160 between the shell 145 and the cover 155. The projections define the edges of the compartments 200 A, B, C, D. The shell 145 includes at least one barrier layer including at least one cavity, the at least one cavity configured to reversibly mate with a surface of at least one of a plurality of sensor modules. In the illustration of FIG. 5, the barrier layer is identical to the shell 145; however, in some embodiments, there is a distinct barrier layer adjacent to the interior or exterior surface of the shell 145. As shown in FIG. 5, the shell 145 includes a barrier layer with a cavity 500 A configured to reversibly mate with the surface of sensor module 150 A. Although FIG. 5 depicts a gap between the surface of the cavity 500 A and the surface of the sensor module 150 A, this gap is present for illustrative purposes in the Figure. In many embodiments, the surface of the cavity 500 A and the surface of the sensor module 150 A would be positioned in direct contact with each other. An adhesive or other fastener in the gap between the surface of the cavity 500 A and the surface of the sensor module 150 A can be included to ensure that the sensor module 150 A is secure relative to the cavity 500 A. As shown in FIG. 5, at least one surface of the sensor module 150 A is configured to align within the corresponding cavity 500 A in the shell 145. Similarly, the sensor modules 150 B, 150 C and 150 D include surfaces configured to reversibly mate with the corresponding cavities 500 B, 500 C and 500 D in the shell 145. Although the cavities 500 A, B, C, D illustrated in FIG. 5 are all substantially the same shape (i.e. rectangular), in some embodiments the shell 145 can include a plurality of cavities 500 of different sizes and shapes to correspond in size and shape to a plurality of sensor modules 150.

Figure 6:
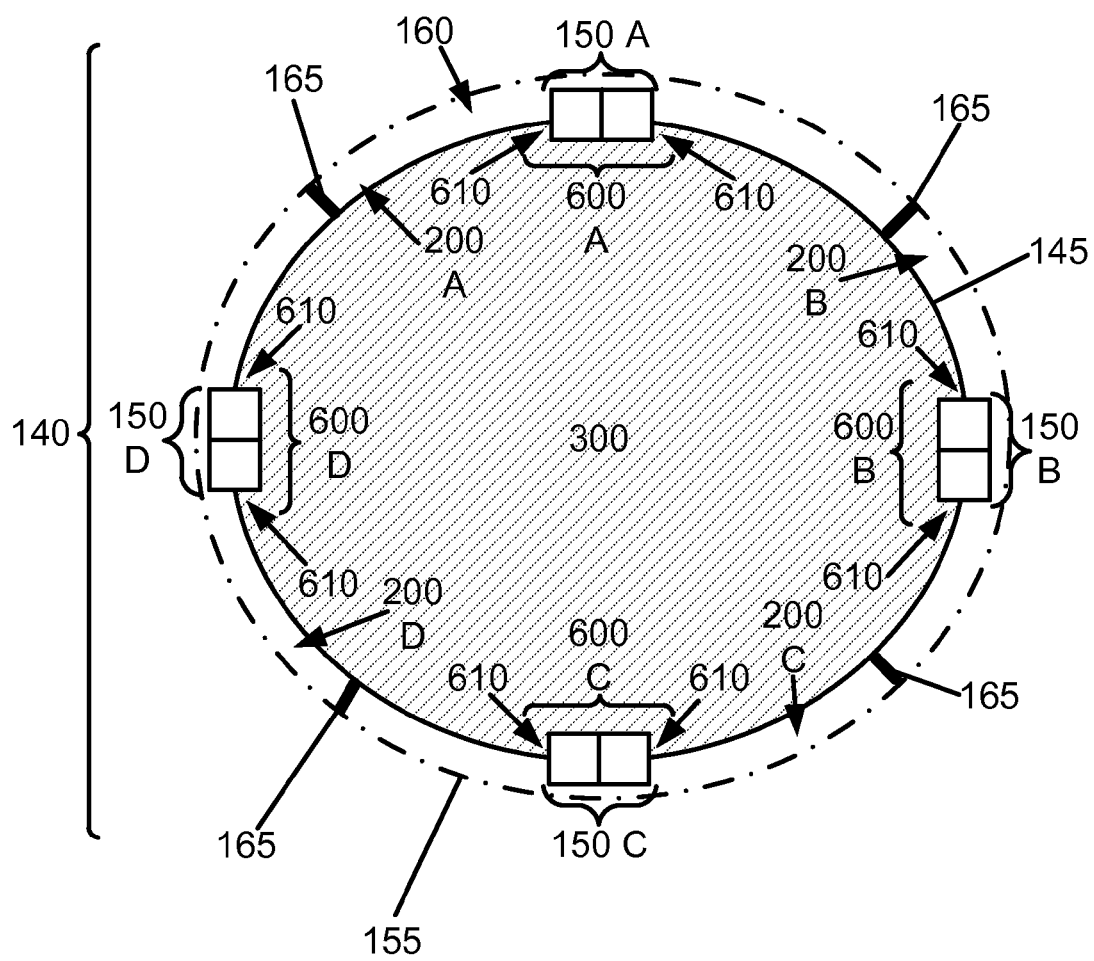
FIG. 6 is a schematic of a breast implant ex vivo in cross-section view.

FIG. 6 illustrates aspects of a breast implant 140 including a plurality of sensor modules 150 A, 150 B, 150 C and 150 D. The breast implant 140 depicted in FIG. 6 is shown in cross-section, a similar view as in FIGS. 3, 4 and 5. The breast implant 140 includes interior viscous material 300. A fluid-permeable cover 155 completely surrounds and envelops the shell 145 with a gap 160 between the shell 145 surface and the cover 155 surface. A plurality of projections 165 extend from an external surface of the shell 145, the projections 165 forming a plurality of compartments 200 A, B, C, D adjacent to the external surface of the shell 145. As shown in FIG. 6, the shell 145 includes at least one barrier layer including at least one aperture 600, the at least one aperture 600 with a rim surface 610 configured to reversibly mate with a surface of at least one of the plurality of sensor modules 150. As shown in FIG.

6, at least one surface of the sensor module 150 A is configured to align within the corresponding rim surface 610 of an aperture 600 A in the shell 145. Similarly, the sensor modules 150 B, 150 C and 150 D include surfaces configured to reversibly mate with the rim surfaces 610 of the corresponding apertures 600 B, 600 C and 600 D in the shell 145. As illustrated in FIG. 6, the shell 145 includes an aperture 600A with rim surface 610 configured to reversibly mate with the outer surface of sensor module 150 A. Similarly, FIG. 6 illustrates that the shell 145 includes a plurality of apertures 600 A, 600 B, 600 C, 600 D, each of which include rim surfaces 610 configured to reversibly mate with the outer surface of a corresponding sensor module 150 A, 150 B, 150 C, 150 D. An adhesive or other fastener can be included on the rim surface 610 to ensure that a sensor module 150 is secure relative to the rim surface 610 of an aperture 600. Although the apertures 600 A, B, C, D illustrated in FIG. 6 are all substantially the same shape (i.e. rectangular), in some embodiments the shell 145 can include a plurality of apertures 600 of different sizes and shapes to correspond in size and shape to a plurality of sensor modules 150.

As illustrated in FIGS. 5 and 6 as well as the associated text, the plurality of sensor modules 150 operably attached to the shell 145 can be modular. For example, a breast implant 140 can include a plurality of cavities 500 in the shell 145 (e.g. as shown in FIG. 5) configured to reversibly mate with the surface of a plurality of sensor modules 150 of different types, allowing substitution of different types of sensor modules 150 with specific breast implants 140 as desired in a specific situation. For example, a standard breast implant 140 with cavities 500 of a standard size and shape can be manufactured and sensor modules 140 inserted as desired to suit a particular medical situation. For example, a breast implant 140 can include a plurality of apertures 600 in the shell 145 (e.g. as shown in FIG. 6) with rim surfaces configured to reversibly mate with the surface of a plurality of sensor modules 150 of different types, allowing substitution of different types of sensor modules 150 with specific breast implants 140 as desired in a specific situation. For example, a standard breast implant 140 with apertures 600 of a standard size and shape can be manufactured and sensor modules 140 inserted as suitable for a particular patient. For example, sensor modules 140 configured to respond to Her2/neu proteins may be included in a breast implant 140 intended for use in a reconstructive surgery with a patient who has a history of a Her2/neu positive breast cancer diagnosis. For example, sensor modules 140 configured to respond to markers of breast cancer tissue abnormalities, such as hypoxia, necrosis and inflammation, may be included in a breast implant 140 intended for use in a augmentation surgery in a person without a history of breast cancer diagnosis. A cover 155 can be added to the breast implant 140 after the specific sensor modules 150 are attached to the shell 145. Although FIGS. 5 and 6 do not specifically illustrate a power source 330, one or more power source can be included, with connections to the sensor modules that are configured to be reversible. For example, if the connection between a power source 330 and a replaceable sensor module 150 includes a wire connection 340, a socket or other connection site can be included on the sensor module 150 at a location configured to mate with the wire connection 340 at the edge of a cavity 500 or aperture 600. For example, one or more power sources 330 can be positioned within an aperture. For example, one or more power sources can be positioned within a cavity.

Figure 7:
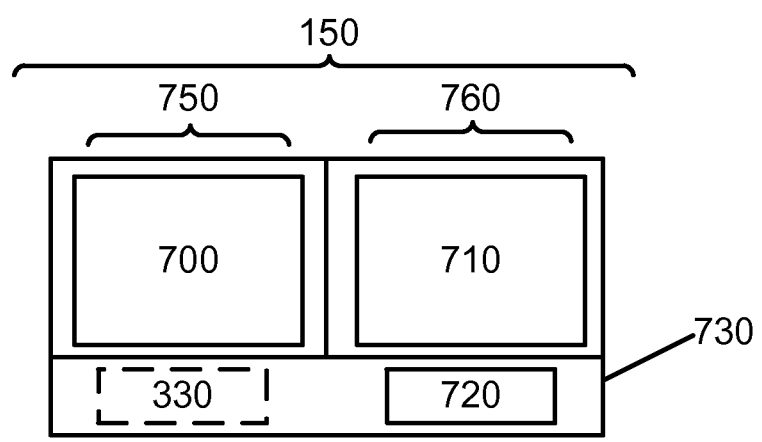
FIG. 7 is a schematic of a sensor module.

FIG. 7 illustrates aspects of a sensor module 150. As illustrated in FIG. 7, the sensor module 150 includes two individual sensor units, 700, 710. In some embodiments, a sensor module 150 can include a single sensor unit or more than two sensor units. Each sensor unit 700, 710 includes a sensor configured to detect at least one analyte. Each sensor can be configured to respond to a specific analyte, or a group of analytes. The individual sensor units 700, 710 illustrated in FIG. 7 can be configured to detect the same or different analytes, depending on the embodiment. The individual sensor units 700, 710 illustrated in FIG. 7 can be configured to detect analytes of different types. For example, a sensor unit 700 can be configured to detect the presence of maspin protein in the fluid originating adjacent to the implant 140 and a sensor unit 710 can be configured to detect the presence of Her2/neu protein in the fluid originating adjacent to the implant 140. In some embodiments, the sensor units 700, 710 in a sensor module 150 can include sensor units that are configured to be activated at different times. For example, the sensor units 700, 710 can include long term analyte sensors, such as described in U.S. Pat. No. 7,577,470, "Long Term Analyte Sensor Array" to Shah et al., which is incorporated herein by reference. See also European Patent Application No. 06718063.8 to Shah et al., "Fabrication of Multi-Sensor Arrays," which is incorporated herein by reference. For example, the sensor units 700, 710 can include a plurality of sensors, each of which are isolated and inactive until an opening is formed in a covering over the respective sensor, such as described in European Patent Application No. 01926347.4, "Microfabricated Devices and Methods for Storage and Selective Exposure of Chemicals," to Santini et al., and U.S. Pat. No. 5,797,898, "Microchip Drug Delivery Devices," to Santini et al., which are each incorporated herein by reference. See also US Patent Application No. 2011/0082356 to Yang et al., "Analyte Sensor Apparatuses Having Interference Rejection Membranes and Methods for Making and Using Them," which is incorporated herein by reference.

In some embodiments, a sensor unit can include a recognition element and a transducer. See, e.g. Bohunicky and Mousa, "Biosensors: The New Wave in Cancer Diagnosis," Nanotechnology, Science and Applications, 4 (2011), which is incorporated herein by reference. A recognition element is configured to detect an analyte. In some embodiments, a recognition element detects an analyte through molecular binding to the analyte. For example, some recognition elements include proteins, antibodies, antibody fragments, aptamers, or nucleic acids that bind to specific analytes. Recognition elements can include, for example, aptamers, molecularly imprinted polymers, antibodies, antibody mimics, or antibody synthetics. A transducer within a sensor unit can convert a signal from the recognition element that an analyte has been detected to an output, such as an electrical output. In some embodiments, the transducer is an electrochemical transducer that converts a chemical signal to an electrical output. In some embodiments, the transducer is an optical transducer that converts an optical signal to an electrical output. In some embodiments, the transducer is responsive to mass change, and converts a mass change into an electrical signal. For example, the transducer can include a piezoelectric element. In some embodiments, the transducer is a calorimetric transducer that converts a thermal signal to an electrical output.

In some embodiments, a sensor module can include a processor. For example, a sensor module can include a micromechanical system (MEMS) device, including a microprocessor and microsensor units. In some embodiments, a sensor module can include an antenna. For example, the antenna can be configured to respond to electromagnetic energy in the radiofrequency (RF) range. In some embodiments, a sensor module can include an energy harvesting unit. For example, a sensor module can include a passive RFID energy harvesting unit. In some embodiments, a sensor module can include a radio frequency identification (RFID) unit. In some embodiments, a sensor module can include a programmable RFID device such as the Wireless Identification and Sensing Platform (WISP). See, for example, Sample et al., "Design of an RFID-Based Battery-Free Programmable Sensing Platform," IEEE Transactions of Instrumentation and Measurement, 57:11, 2608-2615 (2008), which is incorporated herein by reference. In some embodiments, the sensor module can include a switch. For example, the sensor module can include a switch configured to change the state of a processor when an analyte is detected. For example, the sensor module can include a switch configured to enable a transmission unit when an analyte is detected.

In some embodiments, a sensor module includes a plurality of reservoirs. For example, the sensor units can be operably attached to one or more reservoirs configured to provide reagent(s) required by the sensor units during use. For example, the sensor units can be operably attached to one or more reservoirs configured to provide protection to the sensor units during use. Each of the reservoirs can include a removable cover configured to be removed prior to use of that specific reservoir. For example, each of the reservoirs can include a removable cover configured to dissolve slowly over time and thereby provide the internal reagent(s). For example, each of the reservoirs can include a removable cover configured to be removed by a specific signal. See, for example, European Patent Application No. 01926347.4, "Microfabricated Devices and Methods for Storage and Selective Exposure of Chemicals," to Santini et al., and U.S. Pat. No. 7,410,616, "Device for the Controlled Exposure of Reservoir-Based Sensors," to Santini et al., which are each incorporated herein by reference. See also US Patent Application No. 2011/0082356 to Yang et al., "Analyte Sensor Apparatuses Having Interference Rejection Membranes and Methods for Making and Using Them," which is incorporated herein by reference.

The sensor units 700, 710 in a sensor module 150 such as illustrated in FIG. 7 can include a variety of sensor types. In some embodiments, a sensor module 150 includes sensor units 700, 710 of different types. For example, sensor unit 700 can be configured to detect an analyte ("A") and sensor unit 710 can be configured to detect a different analyte ("B"). Sensor units 700, 710 can be selected based on the analyte(s) of interest in a particular embodiment. Sensor units 700, 710 can be selected based on factors such as cost, performance, durability, size and energy requirements. A sensor module 150 can include a recognition element that detects an analyte. In some embodiments, the sensor units 700, 710 in a sensor module 150 can include at least one recognition element. In some embodiments, the sensor units 700, 710 in a sensor module 150 can include sensor units that include chemiresistors. For example, the sensor units 700, 710 in a sensor module 150 can include a chemically sensitive resistor such as described in US Patent Application No. 2006/0034731, "Sensor Arrays for Detecting Analytes in Fluids," to Lewis and Gao, which is incorporated herein by reference. For example, the sensor units 700, 710 can include a chemiresistor-based sensor such as described in US Patent Application No. 2010/0276302, "Chemiresistor for Use in Conducting Electrolyte Solution," to Raguse and Chow, which is incorporated herein by reference. In some embodiments, the sensor units 700, 710 in a sensor module 150 can include a chemical affinity based sensor. In some embodiments, the sensor units 700, 710 in a sensor module 150 can include nanoparticle-based sensor units. For example, the sensor units 700, 710 in a sensor module 150 can include a nanoparticle/nanofiber based chemical sensor such as described in US Patent Application No. 2007/0114138, "Nanoparticle/Nanofiber Based Chemical Sensor, Arrays of Such Sensors, Uses and Method of Fabrication Thereof, and Method of Detecting an Analyte," to Krasteva et al., which is incorporated herein by reference. In some embodiments, the sensor units 700, 710 in a sensor module 150 can include optical-based sensors. For example, the sensor units 700, 710 in a sensor module 150 can include an optical-based sensor with a sensor body that functions as a wave guide. See, for example, U.S. Pat. No. 6,304,766 "Optical-Based Sensing Devices, Especially for In-Situ Sensing in Humans" to Colvin, which is incorporated herein by reference. For example, the sensor units 700, 710 in a sensor module 150 can include an optically-readable array. See, for example, U.S. Pat. No. 7,302,289, "Readable Probe for In-Vivo Use," to Crowley, which is incorporated herein by reference. In some embodiments, the sensor units 700, 710 in a sensor module 150 can include electric or acoustic fields. See, for example, European Patent Application No. 05008128.0, "Implantable Biosensor and Methods for Monitoring Cardiac Health," to Shelchuk, and U.S. Pat. No. 7,223,237, "Implantable Biosensor and Methods for Monitoring Cardiac Health," to Shelchuk, which are each incorporated herein by reference. A sensor module can include a recognition element including at least one aptamer configured to bind to an analyte. In some embodiments, the sensor units 700, 710 in a sensor module 150 can include aptamer-based sensors. See, for example: Lai et al., "Aptamer-Based Electrochemical Detection of Picomolar Platelet-Derived Growth Factor Directly in Blood Serum," Anal. Chem. 79: 229-233 (2007); Lee et al., "Aptamers and Molecular Recognition Elements for Electrical Nanobiosensors," Anal. Bioanal Chem. 390: 1023-1032 (2008); So et al., "Single-Walled Carbon Nanotube Biosensors Using Aptamers as Molecular Recognition Elements," JACS Communications 127: 11906-11907 (2005); and Savran et al., "Micromechanical Detection of Proteins Using Aptamer-Based Receptor Molecules," Anal. Chem. 76:3194-3198 (2004), which are each incorporated herein by reference. A sensor module can include a recognition element including at least one nucleic acid configured to bind to an analyte. In some embodiments, the sensor units 700, 710 in a sensor module 150 can include piezoelectric sensors. See, for example, Tombelli et al., "Piezoelectric Biosensors: Strategies for Coupling Nucleic Acids to Piezoelectric Devices," Methods 37: 48-56 (2005), which is incorporated herein by reference. In some embodiments, the sensor units 700, 710 in a sensor module 150 can include voltammetic sensors. See, for example, Blanco-López et al., "Voltammetric Sensor for Vanillylmanelic Acid Based on Molecularly Imprinted Polymer-Modified Electrodes," Biosensors and Bioelectronics 18: 352-362 (2003), which is incorporated herein by reference. In some embodiments, the sensor units 700, 710 in a sensor module 150 can include field effect transistors. See, for example, Maehashi et al., "Label-Free Protein Biosensor Based on Aptamer-Modified Carbon Nanotube Field-Effect Transistors," Anal. Chem. 79: 782-787 (2007), which is incorporated herein by reference. A sensor module can include a recognition element including at least one antibody configured to bind to an analyte. In some embodiments, the sensor units 700, 710 in a sensor module 150 can include immunosensors. See, for example, U.S. Pat. No. 7,006,858, "Implantable, Retrievable Sensors and Immunosensors," which is incorporated herein by reference. In some embodiments, the sensor units 700, 710 in a sensor module 150 can be configured to release an agent detectable by energy in the infrared region of the spectrum in response to an analyte. See, for example, U.S. Pat. No. 7,964,390, "Sensor System" to Rozakis et al., which is incorporated herein by reference. In some embodiments, a sensor unit 700, 710 can be refreshed or recharged for long-term use.

In some embodiments, the sensor units 700, 710 in a sensor module 150 can include sensor units that include crystalline colloidal array of polymer spheres polymerized within a hydrogel. See, for example, Holtz and Asher, "Polymerized Colloidal Crystal Hydrogel Films as Intelligent Chemical Sensing Materials," Nature 389: 829-832 (1997), which is incorporated herein by reference. In some embodiments, the sensor units 700, 710 in a sensor module 150 can include sensor units that include an integrated biosensor system for the simultaneous detection of a plurality of different types of targets. See, for example, U.S. Pat. No. 6,743,581, "Multifunctional and Multispectral Biosensor Devices and Methods of Use" to Vo-Dinh, which is incorporated herein by reference. In some embodiments, the sensor units 700, 710 in a sensor module 150 can include sensor units that include at least one wireless complementary metal oxide semiconductor (CMOS) sensor. See, for example, US Patent Application Publication No. 2009/0298704 to Anwar, "Wireless CMOS Biosensor," which is incorporated herein by reference. See also: Daniel et al., "Implantable Diagnostic Device for Cancer Monitoring," Biosens. Bioelectron. 24:11, 3252-3257 (2009); and Ling et al., "Implantable Magnetic Relaxation Sensors Measure Cumulative Exposure to Cardiac Biomarkers," Nature Biotechnology 29: 3 273-278, which are each incorporated herein by reference. In some embodiments, the sensor units 700, 710 in a sensor module 150 can include sensor units that include magnetic particles, wherein the extent of aggregation of the magnetic particles are indicative of the presence or absence of an analyte. See, for example, US Patent Application Publication No. 2010/0072994 to Lee and Berry, "NMR Systems for In Vivo Detection of Analytes," which is incorporated herein by reference. In some embodiments, the sensor units 700, 710 in a sensor module 150 can include sensor units that include a hydrogel matrix with sensor particles. See, for example, US Patent Application Publication No. 2010/0331634 to Müller et al., "Hydrogel Implant for Sensing Metabolites in Body Tissue," which is incorporated herein by reference. In some embodiments, the sensor units 700, 710 in a sensor module 150 can include sensor units that include an optical-based sensor including light-absorbing indicator molecules. See, for example, U.S. Pat. No. 6,304,766 to Colvin, "Optical-Based Sensing Devices, Especially for In-Situ Sensing in Humans," which is incorporated herein by reference. In some embodiments, the sensor units 700, 710 in a sensor module 150 can include sensor units that include an optically readable polydeoxy-nucleotide array with integral fluorescence excitation and fluorescence emission channels. See, for example, U.S. Pat. No. 7,302,289 to Crowley, "Readable Probe Array for In-Vivo Use," which is incorporated herein by reference. In some embodiments, a sensor unit 700, 710 can be refreshed or recharged for long-term use. In some embodiments, the sensor units 700, 710 in a sensor module 150 can include sensor units that include a plurality of analyte binding domains, with each binding domain being capable of specifically and reversibly binding to at least one target analyte. See, for example, U.S. Pat. No. 7,951,605 to Pitner and Vonk, "Multianalyte Sensor," which is incorporated herein by reference. In some embodiments, the sensor units 700, 710 in a sensor module 150 can include sensor units that include materials that produce a detectable change when the sensor unit is exposed to an analyte, such as the release of an infrared (IR) detectable dye. See, for example, U.S. Pat. No. 7,964,390 to Rozakis et al., "Sensor System," which is incorporated herein by reference. In some embodiments, the sensor units 700, 710 in a sensor module 150 can include sensor units that include graphene-based nanosensors. See, for example, Mannoor et al., "Graphene-based Wireless Bacteria Detection on Tooth Enamel," Nature Communications, 3:763 doi: 10.1038/ncomms1767 (2012).

In some embodiments, the sensor units 700, 710 in a sensor module 150 can include sensor units utilizing recognition elements that are nucleic acid ligands, such as aptamers, configured to bind to specific target proteins that are analytes. In some embodiments, aptamers can be recognition elements for specific analytes. In some embodiments, aptamers specific to particular analytes can be generated using an in vitro selection process referred to as SELEX (Systematic Evolution of Ligands by Exponential enrichment). See, for example U.S. Pat. No. 5,475,096, "Nucleic Acid Ligands," to Gold et al., and U.S. Pat. No. 5,270,163, "Methods for Identifying Nucleic Acid Ligands," to Gold et al., which are each incorporated herein by reference. In some embodiments, one or more sensor units include chemiresistors with aptamers. Aptamers can be thiol-functionalized during fabrication of a chemiresistor with aptamers configured as functional elements. Thiol-functionalized binding aptamers can be obtained from commercial sources such as Integrated DNA Technology, Inc. (Coralville, Iowa). Examples of a thiol-functionalized aptamers for breast cancer analytes can be found, for example, in Da Pieve et al., "Development of Anti-MUC1 DNA Aptamers for the Imaging of Breast Cancer," Breast Cancer Res, 10(Suppl 2):P62, (2008), which is incorporated herein by reference. The chemoresistor sensor units carrying recognition elements can be configured, for example, to detect analytes that are proteins or protein fragments, such as MUC1 protein, Her2 protein, or PDGF-AA protein (see, e.g., Chourb et al., "Enhanced Immuno-Detection of Shed Extracellular Domain of Her-2/Neu," Sci. Res. 1:4, 325-329 (2009), which is incorporated herein by reference).

As shown in FIG. 7, a sensor module 150 can include a structural region 730. The structural region 730 can be fabricated from a variety of materials, depending on the embodiment. For example, the structural region 730 can be fabricated from a polymer, a silicone-based material, a fabric, or a resin. The structural region 730 can be fabricated from flexible materials, or configured for flexibility. The structural region 730 can be fabricated to be bio-compatible. The structural region 730 can be fabricated to be small and lightweight to minimize added weight on the shell 145 from the sensor modules 150. The structural region 730 can include a base or support for various portions of the sensor module 150. The structural region 730 can include adhesive to affix the sensor module 150 to the surface of a shell of a breast implant. The structural region 730 can include one or more surfaces configured to reversibly mate with a surface of a cavity in a barrier layer in a shell of a breast implant. The structural region 730 can include one or more apertures. The structural region 730 can include an outer shell or cover over the entirety or a part of the various portions of the sensor module 150. For example, one or more areas of the structural region 730 configured to allow analytes to flow from the tissue fluid adjacent to the breast implant into the sensor module 150 can include one or more mesh-like or porous regions. For example, the structural region 730 can include a region of film configured with microchannels to direct fluid to a position adjacent to the sensor units 700, 710. See, for example, U.S. Pat. No. 6,420,622 "Medical Article Having Fluid Control Film," to Johnston et al., which is incorporated herein by reference. For example, the structural region 730 can include a polymeric cover. For example, the structural region 730 can include a cover that can be opened in response to a specific signal, such as described in European Patent Application No. 01926347.4, "Microfabricated Devices and Methods for Storage and Selective Exposure of Chemicals," to Santini et al., which is incorporated herein by reference. For example, the structural region 730 can include a surface configured to interface with a surface of a cover 155 (not shown in FIG. 7).

Although the sensor module 150 illustrated in FIG. 7 includes a structural region 730, in some embodiments a structural module does not include a distinct structural region 730 surrounding the sensor module 150. For example, in some embodiments, the sensor module 150 includes elements that are directly attached to the surface of the shell. For example, in some embodiments, the sensor module 150 includes elements that are embedded within the shell.

The sensor module 150 shown in FIG. 7 includes a unique identifier 720. A unique identifier is configured to identify a particular sensor module 150 from any other sensor modules 150 attached to a shell 145 of a particular breast implant 140. For example, a unique identifier can include an alphanumeric code. For example, a unique identifier can include a positional identifier. For example, a unique identifier can include an electronic code, such as a radio frequency identification (RFID) identifier code. For example, a unique identifier can include an electronic code, such as a binary-based code.

In some embodiments, a sensor module 150 includes a power source 330. The power source 330 can serve as a power source specific to that sensor module 150. The power source 330 can serve as a power source for adjacent or related sensor modules 150 (see, e.g. FIG. 3). The power source 330 can include a capacitor. The power source 330 can include an antenna. The power source 330 can include an antenna operable to store electrical energy received from a power source external to the breast implant. See, for example, U.S. Pat. No. 7,479,886, "Antenna Capacitance for Energy Storage" to Burr, and Sample et al., "Photovoltaic Enhanced UHF RFID Tag Antennas for Dual Purpose Energy Harvesting," 2011 *IEEE International Conference on RFID*, 146-153 (2011), which are each incorporated herein by reference.

A sensor module 150 can include a switch. For example, a switch can be configured to activate circuitry for sending a signal in response to the detection of an analyte. For an example of a switch that can be connected to a sensor, see U.S. Pat. No. 7,411,505 "Switch Status and RFID Tag" to Smith, which is incorporated herein by reference. For example, a sensor module can include a switch configured to activate a power source after an analyte is detected. In some embodiments, a sensor module 150 includes a switch configured to activate a processor. For example, a sensor module 150 can include a switch controlling a processor, so that the processor is activated when the sensor module detects an analyte. In some embodiments, a sensor module 150 includes a switch configured to activate a transmission unit. For example, a sensor module 150 can include a switch controlling a transmission unit, so that the transmission unit initiates a signal when the sensor module detects an analyte.

Figure 8:
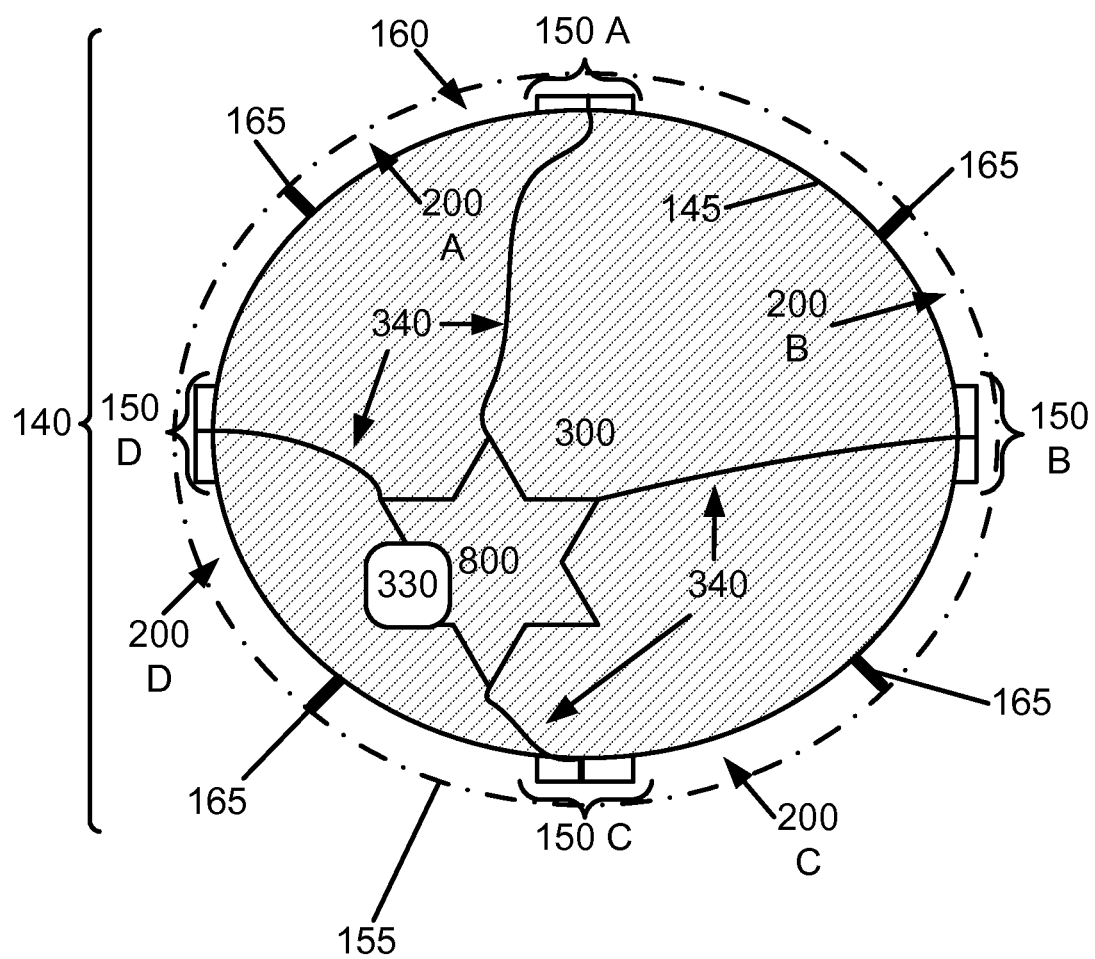
FIG. 8 is a schematic of a breast implant ex vivo in cross-section view.

FIG. 8 illustrates additional aspects of a breast implant 140. The breast implant 140 depicted in FIG. 8 is shown in cross-section, a similar view as in FIGS. 3, 4, 5 and 6. The breast implant 140 includes interior viscous material 300. A fluid-permeable cover 155 completely surrounds and envelops the shell 145 with a gap 160 between the shell 145 surface and the cover 155 surface. A plurality of projections 165 extend from an external surface of the shell 145, the projections 165 forming a plurality of compartments 200 A, B, C, D adjacent to the external surface of the shell 145. Each of the compartments 200 A, B, C, D includes a sensor module 150 A, B, C, D. FIG. 8 shows a breast implant 140 including shell 145 and a plurality of sensor modules 150 A, B, C, D attached to the exterior of the shell 145. Within the interior region of the shell are positioned a processor 800 and an operably attached power source 330. As shown in FIG. 8, the processor 800 is operably attached to the plurality of sensor modules 150 A, B, C, D through a plurality of wire connections 340. Each of the plurality of sensor modules 150 A, B, C, D are attached to a processor 800 with a wire connection 340. The processor 800 is operably attached to a power source 330. In the embodiment illustrated, the power source 330 can be configured to provide power to the sensor modules 150 A, B, C, D as well as the processor 800.

Figure 9:
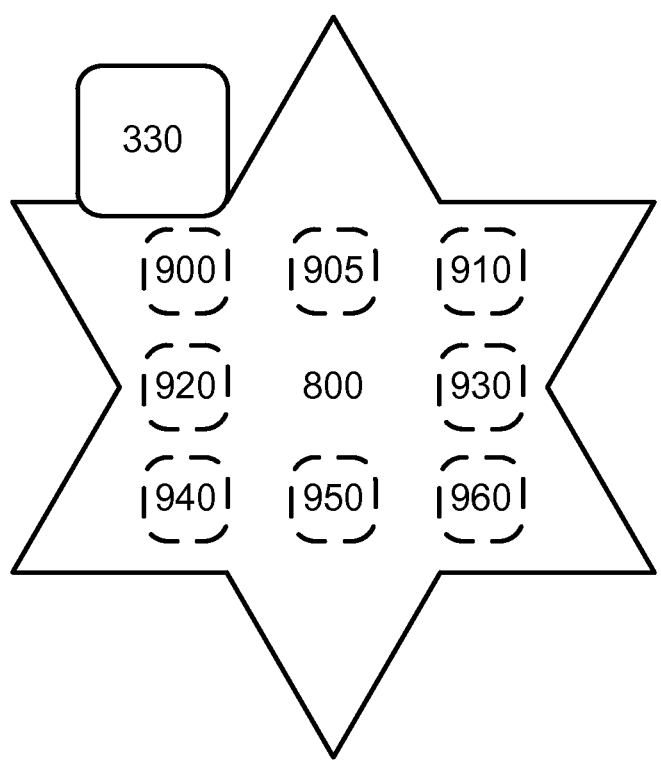
FIG. 9 is a schematic of a processor.

FIG. 9 illustrates additional aspects of a processor 800. In the embodiment shown in FIG. 8, the processor 800 is directly attached to a power source 330. In some embodiments, the processor 800 is indirectly attached to a power source 330, such as attached through a circuit including a sensor module directly attached to the power source 330. The processor 800 can include non-volatile memory 900. The processor 800 can include volatile memory 905. The processor 800 can include circuitry 910, which can be configured to operably connect to the other features of the processor 800. The processor 800 can include logic 920. The processor can include an antenna 930. The antenna 930 can be an antenna configured to operate in the radio frequency (RF) spectrum. Some embodiments can include a self-compensating antenna, such as described in U.S. Pat. No. 7,055,754 to Forster, titled "Self-Compensating Antennas for Substrates having Differing Dielectric Constant Values," which is incorporated herein by reference. An antenna 930 can include dielectric material configured to electrically interact with one or more antennas. See, for example, U.S. Pat. No. 7,055,754 to Forster, titled "Self-Compensating Antennas for Substrates Having Differing Dielectric Constant Values," which is incorporated herein by reference. A processor 800 can include additional features 940, 950, 960, depending on the embodiment. In some embodiments, the processor 800 is indirectly attached to a power source 330, such as attached through a circuit including a sensor module directly attached to the power source 330.

Figure 10:
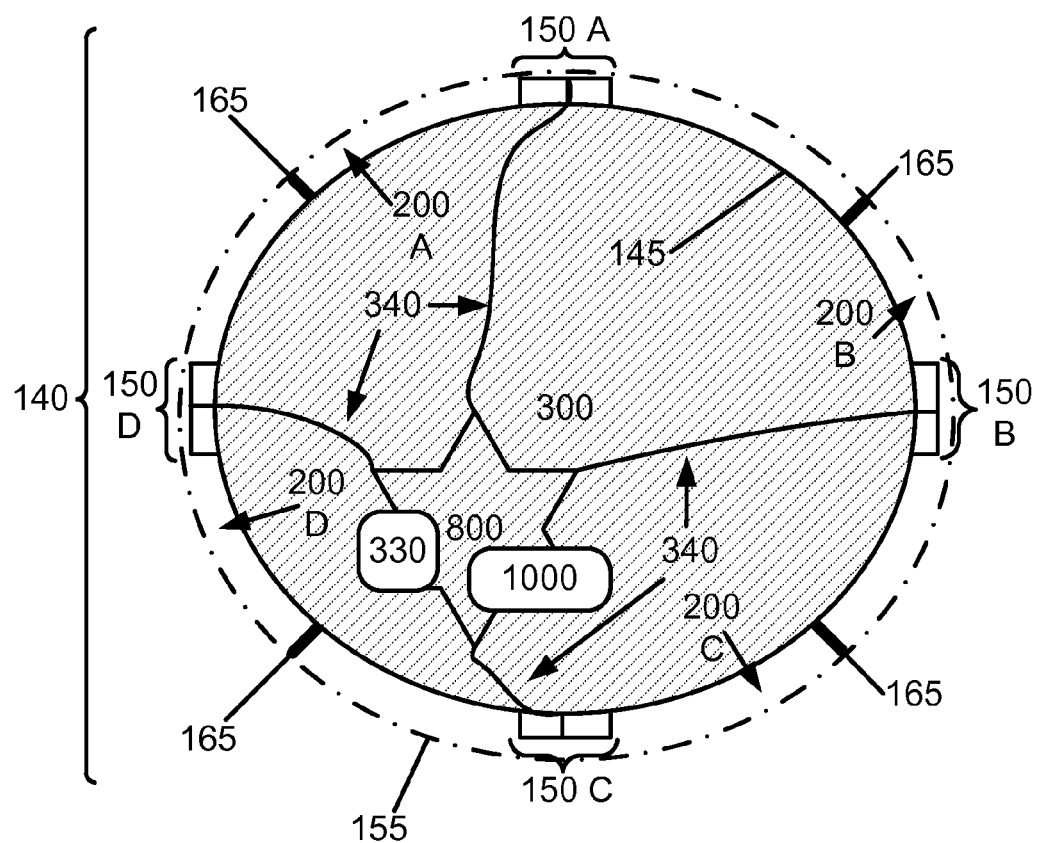
FIG. 10 is a schematic of a breast implant ex vivo in cross-section view.

FIG. 10 illustrates aspects of a breast implant 140. The breast implant 140 depicted in FIG. 10 is shown in cross-section, a similar view as in FIGS. 3, 4, 5, 6 and 8. The breast implant 140 includes interior viscous material 300. A fluid-permeable cover 155 completely surrounds and envelops the shell 145 with a gap 160 between the shell 145 surface and the cover 155 surface. A plurality of projections 165 extend from an external surface of the shell 145, the projections 165 forming a plurality of compartments 200 A, B, C, D adjacent to the external surface of the shell 145. Each of the compartments 200 A, B, C, D includes a sensor module 150 A, B, C, D. FIG. 10 shows a breast implant 140 including a shell 145 and a plurality of sensor modules 150 A, B, C, D attached to the exterior of the shell 145. Within the interior region of the shell are positioned a processor 800 and an operably attached power source 330. As shown in FIG. 10, the processor 800 is operably attached to the plurality of sensor modules 150 A, B, C, D through a plurality of wire connections 340. In some embodiments, the processor can be operably attached to the plurality of sensor modules 150 A, B, C, D through a plurality of fiber-optic connectors. Each of the plurality of sensor modules 150 A, B, C, D are attached to a processor 800 with a wire connection 340. The processor 800 is operably attached to a power source 330.

FIG. 10 shows that the processor 800 is operably attached to a transmission unit 1000. A 'transmission unit," as used herein, is a unit that functions to transmit a signal out of the implant region. In some embodiments, a transmission unit can transmit a signal to a region external from the person carrying the implant, such as to a remote device. In some embodiments, a transmission unit can transmit a signal within the body to a secondary receiver that then transmits a corresponding signal out of the body. A transmission unit 1000 can be configured to transmit a signal in response to an interrogation signal. For example, a transmission unit 1000 can be configured to transmit a signal after receiving an interrogation signal originating from a remote device. A transmission unit 1000 can include a transponder utilizing electromagnetic waves, for example as described in "Fundamental Operating Principles," in Chapter 3 of the *RFID Handbook: Fundamentals and Applications in Contactless Smart Cards and Identification*, Klaus Finkenzeller, John Wiley & Sons, (2003), which is incorporated herein by reference. A transmission unit 1000 can include an oscillator and encoder configured to generate a programmable pulse position-modulated signal in the radio frequency range. See, for example, U.S. Pat. No. 4,384,288 to Walton, titled "Portable Radio Frequency Emitting Identifier," which is incorporated herein by reference. A transmission unit 1000 can include a radio frequency identification device (RFID). A transmission unit 1000 can be configured to be a transmitter of signals in the UHF range. A transmission unit 1000 including an RFID device can be configured to transmit signals in the UHF standard range utilized in a global region, as illustrated in the "Worldwide RFID UHF Map" by Intelleflex Corporation (©2009), which is incorporated herein by reference. A transmission unit 1000 can include a radio frequency identification device (RFID), which can be a passive RFID device, a semi-passive RFID device, or an active RFID device, depending on the embodiment. See, for example, Chawla and Ha, "An Overview of Passive RFID," *IEEE Applications and Practice*, 11-17 (September 2007), which is incorporated herein by reference. A transmission unit 1000 can include a battery-assisted passive RFID device. A transmission unit 1000 can include an optical transmitter unit. A transmission unit 1000 can be configured to transmit at approximately 13.56 megahertz (MHz), or within the ISO 14443 standard parameters. See Patauner et al., "High Speed RFID/NFC at the Frequency of 13.56 MHz," presented at the *First International EURASIP Workshop on RFID Technology*, pages 1-4, 24-25 Sep. 2007, Vienna Austria, which is incorporated herein by reference. A transmission unit 1000 can include a hybrid backscatter system configured to function in an RFID, IEEE 802.11x standard and Bluetooth system. See, for example, U.S. Pat. No. 7,215,976 to Brideglall, titled "RFID Device, System and Method of Operation Including a Hybrid backscatter-based RFID Protocol Compatible with RFID, Bluetooth and/or IEEE 802.11x Infrastructure," which is incorporated herein by reference. A transmission unit 1000 can include a near field communication (NFC) device. A transmission unit 1000 can include a Wireless Identification and Sensing Platform (WISP) device, manufactured by Intel Corporation, such as described in the "WISP: Wireless Identification and Sensing Platform" webpage (downloaded on Oct. 28, 2011) incorporated herein by reference. A transmission unit 1000 can include an infrared (IR) source (approximately 0.74 µm to 300 µm in wavelength). A transmission unit 1000 can include a light source in the visible wavelengths (approximately 380 nm to 740 nm in wavelength).

Figure 11:
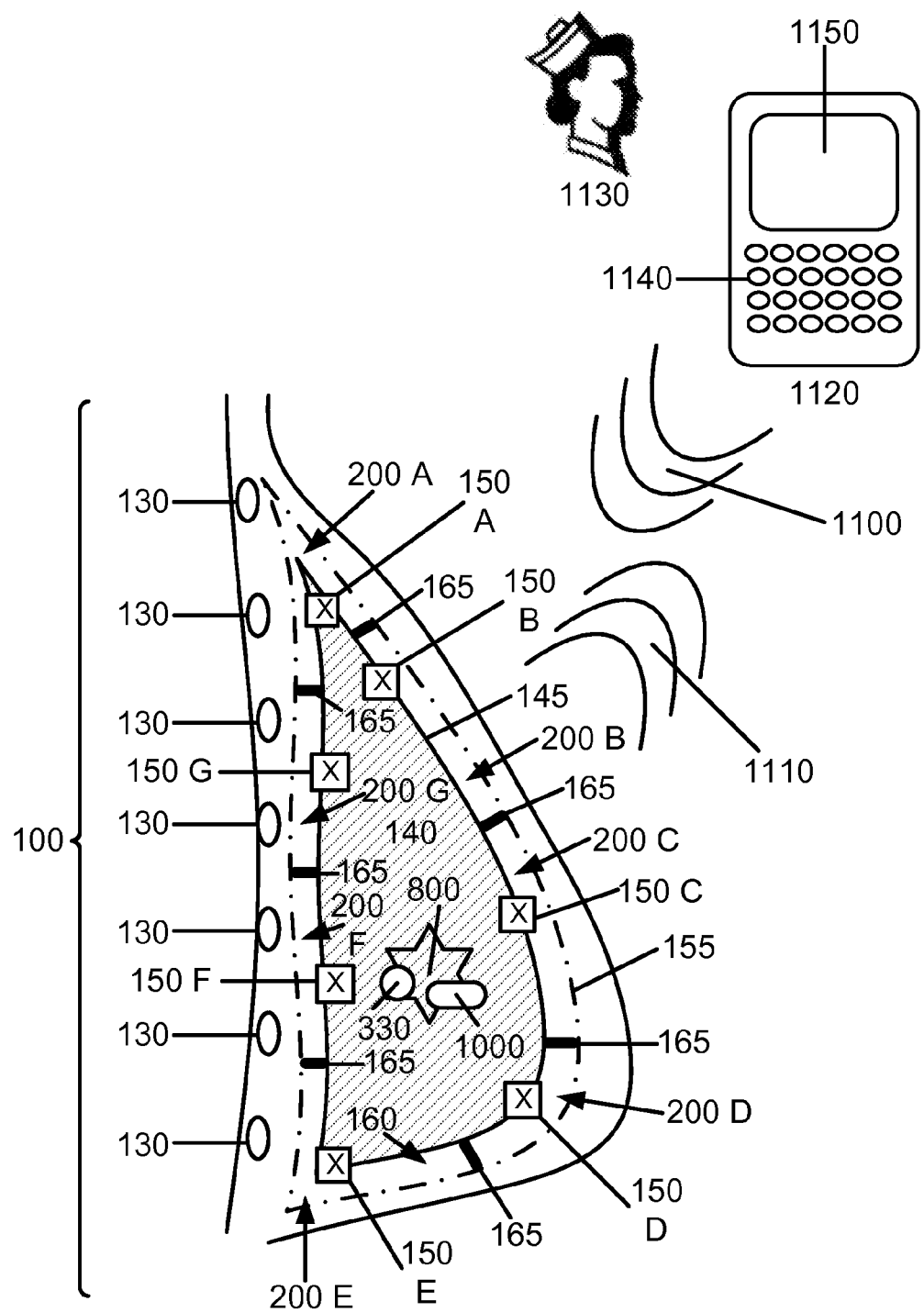
FIG. 11 is a schematic of a breast implant in vivo in cross-section view in communication with a remote device.

FIG. 11 illustrates aspects of a breast implant 140 in use. FIG. 11 depicts a cross-section view of the breast implant 140 in situ within a breast 100. FIG. 11 shows a cross-section view through the side of an individual person, including a cross-section illustration of the individual's ribs 130 in the chest wall. A fluid-permeable cover 155 completely surrounds and envelops the shell 145 with a gap 160 between the shell 145 surface and the cover 155 surface. A plurality of projections 165 extend from an external surface of the shell 145, the projections 165 forming a plurality of compartments 200 A, B, C, D, E, F, G adjacent to the external surface of the shell 145. The projections 165 can be fabricated from the same or similar material as the shell. The projections 165 can be fabricated from a fluid-impermeable membrane, such as one including a plastic polymer. The projections 165 are attached to the outer surface of the shell 145. Each of the compartments 200 A, B, C, D, E, F, G includes a sensor module 150 A, B, C, D, E, F, G. The breast implant 140 includes a plurality of sensor modules 150 A, B, C, D, E, F and G. Each of the sensor modules 150 A, B, C, D, E, F and G is attached to the shell 145 and oriented to detect one or more analytes in a fluid within one of the plurality of compartments 200 A, B, C, D, E, F, G. In the interior of the breast implant 140 is a processor 800, which is attached to a power source 330 and a transmission unit 1000. Although for the purposes of illustration connections are not explicitly shown between the processor 800 and the sensor modules 150 A, B, C, D, E, F and G, such connections are present in the illustrated embodiment. Information regarding the status of the sensors is conveyed from the individual sensor modules 150 A, B, C, D, E, F and G to the processor 800 through connections (not illustrated). The processor 800 then causes a signal 1110 to be sent from the transmission unit 1000 to a remote device 1120. A user 1130, such as a medical professional, operates the remote device 1120. Although user 1130 is shown/described herein as a single illustrated figure, user 1130 can be representative of a human user, a robotic user (e.g., computational entity), and/or substantially any combination thereof (e.g., a user can be assisted by one or more robotic agents) unless context dictates otherwise. In general, the same may be said of "sender" and/or other entity-oriented terms as such terms are used herein unless context dictates otherwise.

The remote device 1120 can be integrated into a multifunctional device, such as a cell phone, medical scanner, nursing personal digital assistant (PDA), or other device. In some embodiments, the remote device 1120 is integrated into a piece of medical equipment. In some embodiments, the remote device 1120 is a stand-alone device. The remote device 1120 can include an indicator unit 1150, such as a display, touchscreen, light indicator, auditory indicator, vibration emitter, or similar units. The remote device 1120 can include a user interface 1140 such as a keyboard, one or more buttons, a touchscreen, or similar units. The remote device 1120 can include a transmitter configured to transmit signals 1100 configured to be received by the breast implant 140. For example, signals 110 transmitted from the remote device 1120 can be configured to be received by the transmission unit 1000. In some embodiments, the signal 1100 may be a radio-frequency wave, an IR wave, or ultrasound.

Although the remote device 1120 is illustrated in FIG. 11 as a distance away from the surface of the breast 100, in some embodiments the remote device 1120 may have an operational range that is no more than approximately 5-10 cm in linear distance. Therefore, in some embodiments the remote device 1120 can be placed in contact with the surface of the breast 100, or in close proximity to the breast 100 (i.e. no more than 10 cm away from the surface), during use.

Figure 12:
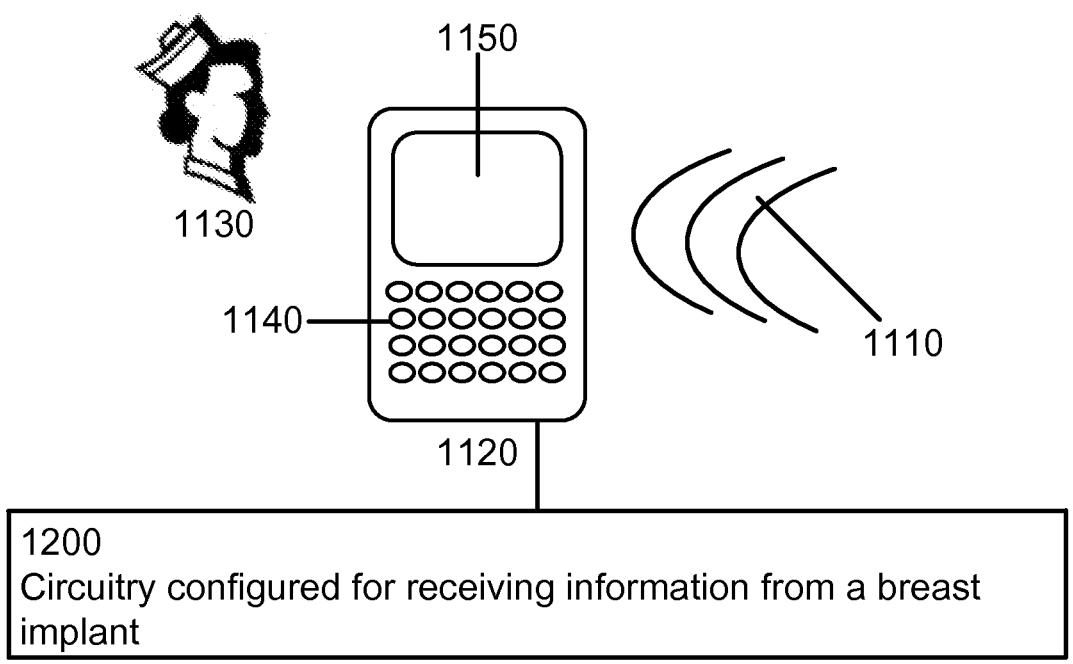
FIG. 12 is a schematic of a remote device.

FIG. 12 illustrates aspects of a remote device 1120. The remote device 1120 is configured to receive signals 1110 from a breast implant in situ (not depicted). The remote device 1120 is operated by a user 1130, such as a medical professional. The remote device 1120 includes an indicator unit 1150 that is a display. The remote device 1120 includes a user interface 1140 that is a keyboard. The remote device 1120 includes circuitry 1200 configured for receiving information from a breast implant. For example, the remote device 1120 can include a receiver. For example, the remote device 1120 can include an antenna. For example, the remote device 1120 can include a processor. For example, the remote device 1120 can include non-volatile memory. For example, the remote device 1120 can include logic. For example, the remote device 1120 can include instructions for operations relating to monitoring information from a breast implant. For example, the remote device 1120 can include look-up tables and other stored information that can be associated with a stored signal, such as the relative location on a breast implant for the sensor module associated with each specific identification code.

Figure 13:
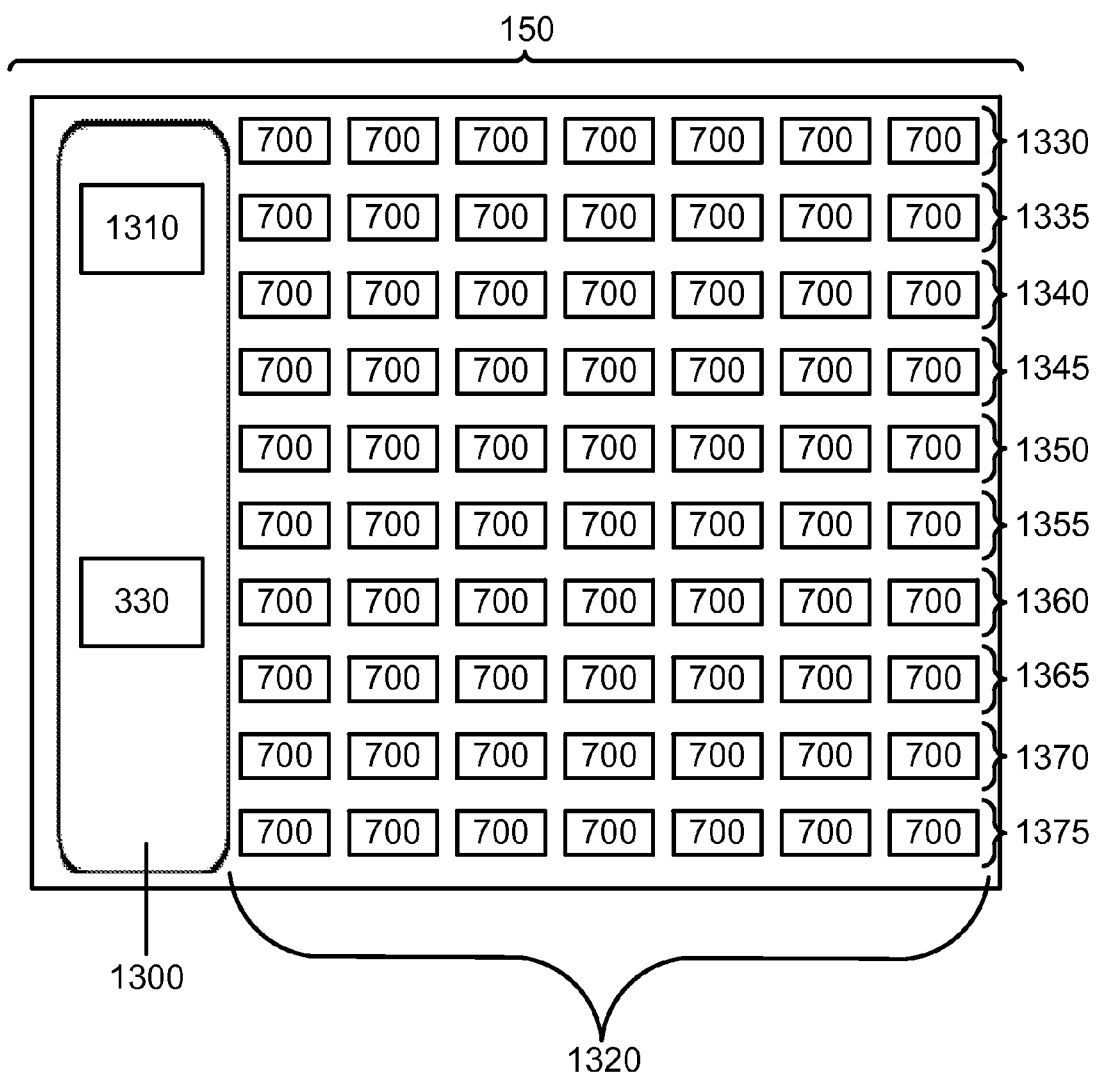
FIG. 13 is a schematic of a sensor module.

FIG. 13 depicts a sensor module 150. In the illustrated embodiment, a circuitry region 1300 of the sensor module 150 is printed on to the surface of a breast implant (as described in Example 1, below). The circuitry region 1300 includes an RFID unit 1310, including an antenna and an identification code specific for the sensor module 150. The circuitry region 1300 includes a power source 330. The sensor module 150 also includes an array 1320 of sensor units 700. Although sensor units 700 are all depicted similarly, they can include sensors configured to identify different analytes (see Example 1). Each sensor unit 700 in the array 1320 is part of a set 1330, 1335, 1340, 1345, 1350, 1355, 1360, 1365, 1370, 1375, 1380, 1385. As shown in FIG. 13, each set 1330, 1335, 1340, 1345, 1350, 1355, 1360, 1365, 1370, 1375, 1380, 1385 of sensor units 700 in the array includes 7 sensor units 700. Each of the sets set 1330, 1335, 1340, 1345, 1350, 1355, 1360, 1365, 1370, 1375, 1380, 1385 can include its own cover (not illustrated). Each cover can be fabricated so as to be disrupted when electrical current is applied across the cover (see e.g., U.S. Pat. No. 7,577,470, "Long Term Analyte Sensor Array" to Shah et al., which is incorporated herein by reference). Each cover can be operably connected to the power source 330.

In some embodiments, a breast implant includes: a shell configured to be substantially filled with a viscous material; a plurality of projections extending from an external surface of the shell, the projections forming a plurality of compartments adjacent to the external surface of the shell; a plurality of sensor modules attached to the shell, each of the sensor modules oriented to detect one or more analytes in a fluid within one of the plurality of compartments, wherein each of the plurality of sensor modules includes a unique identifier; and at least one power source operably attached to the plurality of sensor modules. Some embodiments include a breast implant including a shell configured to be substantially filled with a viscous material and a plurality of projections extending from an external surface of the shell, the projections forming a plurality of compartments adjacent to the external surface of the shell, without a cover attached to the distal ends of the compartments. The compartments can be formed with a end region aperture, the end region aperture distal to the surface of the shell. The compartments can be formed, for example, in shapes such as cups, cones, blocks or bricks along the surface of the implant.

In some embodiments, a breast implant includes: a shell configured to be substantially filled with a viscous material; a plurality of projections extending from an external surface of the shell, the projections forming a plurality of compartments adjacent to the external surface of the shell; a plurality of sensor modules attached to the shell, the sensor modules configured to detect one or more biological analytes arising from biological tissue, the fluid within one of the plurality of compartments; at least one transmission unit attached to the plurality of sensor modules; and at least one power source attached to the plurality of sensor modules and to the transmission unit. In some embodiments, the plurality of sensor modules are positioned on the shell with a distance between the sensor modules. For example, there can be spaces or gaps along the surface of the shell between the sensor modules where the surface of the shell has no attached sensor module. Some embodiments include at least one switch attached to both the at least one transmission unit and the plurality of sensor modules, the at least one switch configured to activate the transmission unit in response to a signal from one or more of the sensor modules.

A method of monitoring information from a breast implant, such as those described herein, includes: receiving first information from a first sensor module attached to a shell of a breast implant within an individual, wherein the first information includes a first unique sensor module identifier and sensor data from the first sensor module; receiving second information from a second sensor module attached to the shell of the breast implant within the individual, wherein the second information includes a second unique sensor module identifier and sensor data from the second sensor module; forming an initial record from the first information and the second information; calculating deviation limits regarding the initial record; setting deviation parameters based on the deviation limits and a predetermined set of standards; saving the initial record and the deviation parameters in memory in a computing device; receiving third information from the first sensor module attached to the shell of the breast implant within the individual, wherein the third information includes the first unique sensor module identifier and sensor data from the first sensor module; receiving fourth information from the second sensor module attached to the shell of the breast implant within the individual, wherein the fourth information includes the second unique sensor module identifier and sensor data from the second sensor module; updating the initial record with the third information and the fourth information; saving the updated record in memory in the computing device; comparing the updated record to the initial record and to the deviation parameters; and indicating if the updated record is within the deviation parameters of the initial record. Some embodiments of the method of monitoring information from a breast implant include: receiving fifth information from the first sensor module attached to the shell of the breast implant within the individual, wherein the fifth information includes the first unique sensor module identifier and sensor data from the first sensor module; receiving sixth information from the second sensor module attached to the shell of the breast implant within the individual, wherein the sixth information includes the second unique sensor module identifier and sensor data from the second sensor module; updating the initial record with the fifth information and the sixth information; saving the updated record in memory in the computing device; comparing the updated record to the initial record and to the deviation parameters; and indicating if the updated record is within the deviation parameters of the initial record. This method can be carried out, for example, by a remote device. In some embodiments, the deviation parameters include no information or insufficient information from at least one sensor module.

In some embodiments, a method of monitoring information from a breast implant includes: sending a signal from a transmission unit attached to one or more sensor modules attached to a breast implant in vivo, wherein the signal contains information regarding the detection of one or more biological analytes by the one or more sensor modules. The signal can be received, for example, by a remote device. Information regarding the received signal can be processed, for example, by a remote device or by a remote computing device. A display including at least a portion of the processed information can be initiated by the remote device. A display including at least a portion of the processed information can be initiated by the remote device. The signal can be saved in memory in a remote device or in a remote device. Processed information regarding the signal can be saved in memory in a remote device or in a remote device. In some embodiments, a detection result for each of the one or more sensor modules includes a positive result, a negative result, or a null result. For example, a positive result can indicate the detection of an analyte by a specific sensor module. For example, a negative result can indicate no detection of an analyte by a specific sensor module. For example, a null result can indicate no information, or insufficient information, regarding detection of an analyte by a specific sensor module.

In some embodiments, a method of monitoring information from a breast implant includes: sending, from a remote device, a query signal to at least one transmission unit attached to a breast implant in vivo, the at least one transmission unit attached to one or more sensor modules configured to detect biological analytes in fluid from biological tissue; receiving, from a remote device, a response signal from the at least one transmission unit attached to the breast implant, the response signal including information from the one or more sensor modules; processing, in a computing device, the response signal to identify information from the one or more sensor modules; and identifying, for each of the one or more sensor modules, a detection result and a unique identifier. In some embodiments, the detection result for each of the one or more sensor modules includes a positive result, a negative result, or a null result. For example, a positive result can indicate the detection of an analyte by a specific sensor module. For example, a negative result can indicate no detection of an analyte by a specific sensor module. For example, a null result can indicate no information, or insufficient information, regarding detection of an analyte by a specific sensor module. Some embodiments include initiating a display of the detection result and the unique identifier for at least one of the sensor modules. For example, initiating a display can include initiating a display on a computer screen or touchpad. For example, initiating a display can include initiating a printout. Some embodiments include initiating a graphic display of the breast implant, the graphic display including a position for each of the sensor modules and the detection result for at least one of the sensor modules. For example, initiating a graphic display of the breast implant can include initiating a diagram or illustration of the breast implant on a computer screen, the graphic display including representations of the sensor modules, and the detection result for at least one of the sensor modules. For example, initiating a graphic display of the breast implant can include initiating a diagram or illustration of the breast implant created as a computer printout. Some embodiments include saving at least one result in a remote device or a remote computing device. Some embodiments include saving, for each of the one or more sensor modules, a detection result in a remote device or a remote computing device. Some embodiments include saving the response signal in a remote device or a remote computing device.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled, implemented, translated, and/or converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein, "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein may be implemented in an analog or digital fashion or some combination thereof.

At least a portion of the devices and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

The herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. Such terms (e.g. "configured to") can generally encompass active-state components and/or inactive-state components and/or standby-state components, unless context requires otherwise.

While particular aspects of the present subject matter described herein have been shown and described, it will be apparent that, based upon the teachings herein, changes and modifications may be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one would understand the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

EXAMPLES

Example 1

A Breast Implant System Constructed with Ink-Jet Printing and Including Multiple Sensor Modules A patient has a total reconstruction of the breast employing a breast implant system. The breast implant system includes a gel-filled breast implant prostheses containing multiple long-lived sensor modules to monitor the tissues surrounding the implant for any new or recurrent breast cancers that may arise. The long-lived sensor modules detect analytes that are breast cancer markers and include a power source, a transmitter, and an identification code for each sensor module. The implant system also includes an external, remote device with a receiver operable to receive transmissions from the sensor modules and to alert the patient and medical personnel if breast cancer markers are detected.

The breast implant prosthesis is a gel-filled hemispherical or crescent-shaped implant with a shell. The implant includes, on the surface of the shell, sensor modules able to detect analytes that are breast cancer markers. The flexible gel-filled implant is fabricated by forming an exterior shell from a silicon elastomer using a mold. The exterior shell is configured to be filled with a viscous material, such as a gel. Methods and compositions to make elastomeric breast prostheses that can be filled with gel are described (see e.g., U.S. Pat. No. 8,043,373 "All-Barrier Elastomeric Gel-Filled Breast Prosthesis," to Schuessler and Powell, which is incorporated herein by reference). For example, the exterior or outer shell may be formed from polydimethylsiloxane containing approximately 15 mole percent diphenylsiloxane (polysiloxanes are available from NuSil Technology, Carpenteria, Calif.). A two-piece rotational mold with a liner may be used to cast the outer shell. A hemispherical seamless, breast implant shell with a wall thickness of approximately 0.456 mm and a base diameter of approximately 12 cm may be manufactured with a rotational mold (see e.g., U.S. Pat. No. 8,043,373, Ibid.). The shell can be filled at a later time with silicone gel (see e.g., U.S. Pat. No. 8,043,373, Ibid.). Multiple sensor modules able to detect analytes that are breast cancer markers are fabricated on the surface of the implant shell to monitor the tissue exudates and interstitial fluids surrounding the implant.

Sensor modules are printed on the surface of the breast implant shell to detect multiple analytes and, therefore, different biomarkers associated with breast cancer. Long-lived sensor modules which signal electronically when they encounter analytes are deposited on the implant shell surface by an ink jet printing process. Methods and materials to fabricate long-lived analyte sensor modules are described (see e.g., U.S. Pat. No. 7,577,470, "Long Term Analyte Sensor Array" to Shah et al., and US Patent Application No. 2010/0276302, "Chemiresistor for Use in Conducting Electrolyte Solution," to Raguse and Chow, which are each incorporated herein by reference). For example chemiresistor sensor units may be printed on the polysiloxane shell using an aerosol-jet printer (see e.g., U.S. Pat. No. 7,485,345, "Apparatuses and Methods for Maskless Mesoscale Material Deposition," to Renn et al. which is incorporated herein by reference). Initially, gold aerosols are printed to form parallel band electrodes that are approximately 3 mm long and 5 μm wide separated by a gap of approximately 5 μm. Chemiresistor sensor units are printed using dimethylamino pyridine (DMAP) coated gold nanoparticles (see e.g., U.S. Patent Appl. 2010/0276302, Ibid.) to create a circular nanoparticle film approximately 300 µm in diameter which coats a portion of both bands of the gold band electrodes. Next a ligand containing a thiol group is added to the DMAP-gold particles to bind analyte. For example, the DMAP-gold nanoparticles are exposed to hexanethiol gas to yield a functional chemiresistor.

Additional electronic components of the sensor module can include: a potentiostat; a battery; a RFID tag; and integrated circuitry. All are printed onto the polysiloxane shell. Methods and materials to print metal traces, inductive coils, interdigitated capacitors, resistor terminations and antennas are described (see e.g., U.S. Pat. No. 7,485,345, Ibid.). Additionally a battery is printed onto the shell attached to each sensor module using known methods and materials (see e.g., U.S. Pat. No. 7,129,166, "Method of Forming an Electronic Device," to Speakman which is incorporated herein by reference). For example, a battery can be printed onto the polysiloxane shell by layering Li—Al to form the negative electrode, polyimide to form a containment well, $LiBF_4$ as an electrolyte separator, and lastly a metallic positive electrode. The layered battery can be coated with acrylate to form a barrier layer over the battery.

A RFID unit that includes antennas and circuitry to receive and transmit radio frequency signals that identify each sensor module on the breast implant is fabricated on the implant shell. The RFID unit can be constructed by printing conductive ink (e.g., polymer with flecks of silver) to create circuitry. Conductive ink is used to print RFID antennas and to connect electronic components on the device. For example, an integrated circuit defining the RFID circuitry for the device is printed on the substrate with conductive epoxy in connection with the conductive ink. The antenna can be a dipole antenna with a capacitor built in to store some of the electrical energy harvested from incident radio waves. The device can have a transmit circuit and a receive circuit to control radio wave communications through the antenna, a power harvester circuit to provide power to the device and a control circuit. Encapsulating epoxy material is used to cover the integrated circuit, the conductive ink and conductive epoxy. Methods and materials to construct RFID tags connected to sensors are described (see e.g.: U.S. Pat. No. 7,479,886, "Antenna Capacitance for Energy Storage," to Burr; and U.S. Pat. No. 7,411,505, "Switch Status and RFID Tag," to Smith et al., which are each incorporated herein by reference). The RFID device with an antenna for transmitting signals to a RFID reader can be constructed with circuitry able to send an identification signal that includes location information, and to transmit an alert when an analyte that is a breast marker is detected (see e.g., Sample et al., "Design of an RFID-Based Battery-Free Programmable Sensing Platform," *IEEE Trans. Instr. Meas.* 57: 2608-2615, (2008) which is incorporated herein by reference).

Sensor modules are printed over the surface of the implant shell to detect analytes that are breast cancer markers arising in breast tissue near exterior surfaces of the implant. For example, a hemispherical breast implant shell with a base diameter of approximately 12 cm will have a total surface area of approximately 300 $cm^2$, which can have approximately 50 to 100 sensor modules printed with approximately 3 cm to 6 cm between the midpoints of each sensor module and uniformly distributed over the surface of the implant. The chemiresistor sensor units are fabricated to detect different analytes, and, therefore, multiple breast cancer markers. Different thiol ligands and thiol ligand mixtures are used to functionalize the nanoparticle films to create distinct chemiresistor sensor units responsive to different breast cancer markers. For example, chemiresistor sensor units containing DMAP-gold nanoparticle films are functionalized by exposure to different ligands (e.g., 1-hexanethiol and 4-mercaptophenol) and to mixtures of these ligands that modulate the sensor unit response to different analytes (see e.g., chemiresistor sensors responsive to the analytes, toluene and ethanol, in U.S. Patent Appl. 2010/0276302 Ibid.). Multiple chemiresistor sensor units functionalized with different thiol ligands and ligand mixtures may be screened with breast cancer markers to identify sensor units responsive to the breast cancer markers. Thiol-functionalized binding aptamers can be obtained from commercial sources such as Integrated DNA Technology, Inc. (Coralville, Iowa). For example, a panel of 7 different metabolites associated with breast cancer may be screened to identify responsive chemiresistor sensor units. Increased levels of the metabolites formate, histidine, proline, choline, glutamic acid, N-acetylglycine, and 3-hydroxy-2-methyl-butanoic acid are correlated with the recurrence of breast cancer (see e.g., Asiago et al., "Early Detection of Recurrent Breast Cancer Using Metabolite Profiling," *Cancer Research* 70: 8309-8318, 2010 which is incorporated herein by reference).

Sensor modules can contain replicate sets of different chemiresistor sensor units which respond to different breast cancer markers (see FIG. 13). Moreover, the replicate sensor units can be protected with covers that can be removed as needed to monitor breast cancer markers over several years. For example, sensor modules containing multiple sets of sensor units for 7 breast cancer markers (see FIG. 13) may be covered with an analyte sensor membrane (e.g., a thin gold foil) that protects the sensors from exposure to interstitial fluid and cells. When a set of sensor units becomes nonfunctional, i.e., no longer signals, it may be deactivated and a new set of sensor units may be activated by disrupting the protective membrane and engaging the circuitry to the new set of sensor units. The protective membrane is disrupted by the application of an electric current or potential which disrupts the gold foil and exposes the set of sensor units to the surrounding interstitial fluid and tissues (see e.g., U.S. Pat. No. 7,577,470 Ibid.). Replicate sets of sensor units, each containing 7 different chemiresistor sensor units configured to detect analytes that are breast cancer markers, can be sequentially exposed to monitor the regions surrounding the breast cancer implant over a period of approximately 5 years.

The breast implant with multiple sensor modules printed onto its surface is filled with an elastic silicone gel and treated with a coating to reduce encapsulation of the implant and to promote vascularization of the surrounding tissue. Following molding and printing of the breast implant shell with multiple sensor arrays on the shell surface, a silicone gel is injected into the implant through an orifice at the base of the implant. Methods and materials to inject the silicone gel and to seal the orifice with siloxane elastomer are described (see e.g., U.S. Pat. No. 8,043,373 Ibid.).

Finally, to prevent fibrous capsule formation and to promote vascularization around the breast implant, a semiporous membrane is used to coat the implant. For example, a membrane of Gore® Teflon (available from W. L. Gore & Associates, Inc., Newark, Del.) with a pore size of approximately 3 µm is used to coat the breast implant and to promote a vascularized interface with the implant and to prevent capsule formation (see e.g., U.S. Pat. No. 5,800,529 to Brauker et al., "Close Vascularization Implant Material," which is incorporated herein by reference).

The breast implant system including the breast implant prosthesis with multiple, distributed sensor modules and an external, remote device including a receiver is used to reconstruct the patient's breast and to monitor tissue exudates and interstitial fluids for breast cancer markers. The remote device can be a cell phone which is configured to send signals to control the sensor units (e.g., activating specific sensor units distributed over the surface of the breast implant shell) and receive signals initiated by the sensor modules when changes in breast cancer analytes are detected. The cell phone may alert the patient and or the patient's physician when breast cancer analytes are detected or sensor units become dysfunctional or the system is otherwise in need of attention.

Example 2

A Breast Implant System for Breast Augmentation Including Sensor Modules with Attached RFID Units for Transmission of Sensor Module Information A patient undergoes breast augmentation surgery employing a breast implant system that includes breast implant prostheses with sensor modules able to monitor for cancer biomarkers in tissue exudates and interstitial fluids surrounding the breast implants. The breast implant system detects shed or secreted breast cancer analytes with a network of sensor modules (see FIG. 2) distributed on the surface of the implant. The sensor modules signal wirelessly to an external, remote device when interrogated by the device, and the remote device alerts the patient and the patient's medical team when analytes that are breast cancer biomarkers are detected.

The breast implant prosthesis shell structure is fabricated as described in Example 1. Sensor modules configured to detect breast cancer analytes of interest are fabricated containing electrochemical sensors with aptamer-based recognition elements. Methods to select and produce aptamers (i.e., oligonucleotides with high affinity binding to molecular targets such as breast cancer antigens) are known (see e.g., U.S. Pat. No. 5,475,096, "Nucleic Acid Ligands," to Gold, which is incorporated herein by reference). The construction of electrochemical sensors using microfabrication methods and employing aptamers to recognize specific biomolecules has been described. See e.g.: U.S. Pat. No. 8,145,434, "Method and Apparatus for Forming a Homeostatic Loop Employing an Aptamer Biosensor," to Shachar et al.; Lee et al., "Aptamers as Molecular Recognition Elements for Electrical Nanobiosensors," *Anal. Bioanal. Chem.* 390: 1023-1032, (2008); and U.S. Pat. No. 8,138,005 "Method for Fabricating Novel High-Performance Field-Effect Transistor Biosensor Based on Conductive Polymer Nanomaterials Functionalized with Anti-VEGF Adapter," to Jang et al. which are each incorporated herein by reference. For example, aptamers can be selected which bind with high affinity and specificity to breast cancer biomarker proteins, such as those produced by HER2 expressing ("HER-2+") cells (see, e.g.: Thiel et al., "Delivery of Chemo-Sensitizing siRNAs to HER2+-Breast Cancer Cells Using RNA Aptamers," Nucleic Acids Research, doi: 10.1093/nar/gks294, 1-19 (2012) and the Supplementary Methods appendix thereof, including the aptamer sequences in Supplementary Table 1 and International Patent Application No. WO2011/142970, "HER2 Nucleic Acid Aptamers," to Gingrande et al., which are each incorporated herein by reference), For example, aptamers can be selected which bind with high affinity and specificity to breast cancer biomarker proteins, such as those produced by HER3 expressing cells. For example, aptamers configured to specifically bind to HER3 proteins expressed from breast cancer cells have been described (see, e.g.: Chen et al., "Inhibition of Heregulin Signaling by an Aptamer that Preferentially Binds to the Oligomeric Form of Human Epidermal Growth Factor Receptor-3," PNAS 100(16), 9226-9231 (2003), which is incorporated herein by reference).

Each sensor unit (see FIG. 7) can be fabricated to include multiple electrodes with different aptamers bound. For example, aptamers that specifically recognize HER2 proteins, HER3 proteins and VEGF (see: Thiel et al., ibid; International Patent Application No, WO2011/142970, ibid.; Chen et al., ibid; and U.S. Pat. No. 8,138,005 to Jang et al., ibid, which are each incorporated by reference herein) can be immobilized on different electrodes in the same sensor unit. The sensor modules can contain multiple electrodes coated with capture reagents, i.e., aptamers, to form capacitive plates. Aptamers can be attached to the electrodes using a chemical linker, (e.g., succinic anhydride) which first bonds to the electrodes using amino-sialanization and then covalently couples with the aptamers during fabrication. The sensor modules include electronic components which form a capacitance detector circuit. The capacitance detector circuit can include: an amplifier buffer, a current to voltage amplifier, resistors, and integration circuits. Binding of biomolecules, e.g., proteins, to the immobilized aptamers changes the impedance at the electrode-solution interface, and changes in impedance can be correlated with the amount of protein analyte bound to the immobilized aptamers (see e.g., U.S. Pat. No. 8,145,434, Ibid.).

The sensor modules (see FIG. 7) configured to detect breast cancer analytes are machined on silicon chips and each include transmission units with RFID units and related circuitry. Fabrication of RFID devices with integrated sensors as microchips approximately 2 cm×2 cm has been described (see e.g., Sample et al., "Design of an RFID-Based Battery-Free Programmable Sensing Platform," *IEEE Trans. Instr. Meas.* 57: 2608-2615, (2008) which is incorporated herein by reference). For example, sensors requiring less than approximately 500 µA of surface space can be integrated and empowered with an RFID device. Each RFID unit is configured to provide wireless communication with a remote device including an external RFID reader. Each RFID unit is configured to harvest power from a signal transmitted from the remote device to empower the sensor modules (i.e., a "passive RFID"). Each RFID unit is configured to transmit a signal identifying the specific RFID unit, and by extension, the attached sensor module. Each RFID unit includes at least one antenna and associated circuitry to receive and transmit radio frequency signals. Methods and materials to construct RFID units with antennas, transmitters, and power harvesters are described (see e.g: U.S. Pat. No. 7,479,886, "Antenna Capacitance for Energy Storage," to Burr; and U.S. Pat. No. 7,411,505, "Switch Status and RFID Tag," to Smith et al., which are each incorporated herein by reference). The antenna can be a dipole antenna with a capacitor built in to store some of the electrical energy harvested from incident radio waves. The device can include a transmit circuit and a receive circuit to control radio wave communications through the antenna, a power harvester circuit to provide power to the device and a control circuit. The RFID unit can be constructed with circuitry to send an identification signal for that unit, and to transmit an alert when the sensor module detects the analyte.

The sensor modules with aptamer-based sensors and RFID devices are attached to the shell of the breast implant in a uniformly distributed network. The sensor units can be attached, for example, using an adhesive. For example, a hemispherical breast implant shell with a diameter of approximately 12 cm will have a total surface area of approximately 300 cm$^2$ and can include approximately 50 to 100 sensor units attached approximately 3 to 6 cm apart and uniformly distributed over the surface of the implant.

Sensor modules contain multiple, replicate aptamer-based sensor units able to detect a set of breast cancer markers. For example, each sensor module can include 56 replicate sensor units with each sensor unit detecting 3 different cancer analytes. See FIG. 13. Sensor modules containing multiple sensor units have been described (see e.g., U.S. Pat. No. 7,577,470, Ibid). The 56 sensor units present on each sensor module can be protected with covers that can be individually removed as needed to monitor breast cancer antigens over several years. For example, the individual sensor units can be covered with analyte sensor membranes (e.g., thin gold foil) that protect the sensors from interstitial fluid, cells, and biofouling. When a new sensor unit is needed on a sensor module, the protective membrane over one sensor unit is removed by the application of an electric current which disrupts the gold foil cover and exposes the new sensor unit to surrounding interstitial fluid and tissues (see e.g., U.S. Pat. No. 7,577,470 Ibid.). Replicate sensor units for breast cancer markers can be sequentially exposed in order to monitor the regions surrounding the breast cancer implant over a period of approximately 5 years. If a sensor becomes nonfunctional, i.e., no longer signals, a signal can be received from a remote device that initiates deactivation of the nonfunctional sensor unit and disruption of the protective membrane to expose a new sensor unit as well as engaging circuitry to activate the new sensor unit.

As described above in FIG. 1, the breast implant shell is filled with an elastic silicone gel and treated with a coating to reduce encapsulation of the implant and to promote vascularization of the surrounding tissue. Following molding of the breast implant shell and attachment of multiple sensor modules on the shell surface with an appropriate adhesive, a silicone gel is injected into the implant through an orifice at the base of the implant. Methods and materials to inject the silicone gel and to seal the orifice with siloxane elastomer are described (see e.g., U.S. Pat. No. 8,043,373 Ibid.).

The breast implant system including the breast implant prostheses with multiple sensor modules is used to aesthetically augment the individual's breasts and also used in combination with a remote device including an external RFID reader to functionally monitor tissue exudates and interstitial fluids for breast cancer analytes. The remote device that includes an external RFID reader can be part of a cell phone. The remote device that includes an external RFID reader can send signals to control the sensor modules (e.g., activating specific sensor units distributed over the surface of the breast implant shell) and receive signals from the sensor modules when changes in breast cancer markers are detected. The cell phone can alert the patient and the patient's physician when analytes that are breast cancer markers are detected or when sensor modules become dysfunctional or need attention.

Example 3

A Breast Implant System with Directed Flow Configured for Breast Reconstruction and Monitoring of Interstitial Fluids for Analytes that are Breast Cancer Biomarkers A patient with breast cancer undergoes a total mastectomy of the affected breast, and after suitable medical treatment the breast is reconstructed with a breast implant system. The breast implant system includes a gel-filled breast implant prostheses including multiple long-lived sensor modules configured to monitor the tissues surrounding the implant for any new or recurrent breast cancers that may arise. The breast implant includes an enveloping membrane including microchannels configured to direct interstitial fluids surrounding the implant to positions adjacent to sensor modules on the implant shell. The long lived sensor modules are configured to detect analytes that are breast cancer markers. The long lived sensor modules each include a power source, a transmitter, an identification code and a unique identifier. The implant system also includes a remote device with an external receiver configured to receive transmissions from the sensor modules and to alert the patient and medical personnel if breast cancer markers are detected.

The breast implant prosthesis shell with attached sensor modules is fabricated as described in Example 1. Multiple analyte sensor modules are printed on the surface of the breast implant shell and configured to detect analytes associated with breast cancer.

Additional electronic components of the sensor module can include: a potentiostat; a battery; a RFID unit; and integrated circuitry. All components are printed onto the polysiloxane shell of the breast implant. Methods and materials to print metal traces, inductive coils, interdigitated capacitors, resistor terminations and antennas are described (see e.g., U.S. Pat. No. 7,485,345 Ibid.). Additionally, at least one battery is printed onto the shell and attached to each sensor module using known methods and materials (see e.g., U.S. Pat. No. 7,129,166, "Method of Forming an Electronic Device," to Speakman which is incorporated herein by reference). See also Example 1.

Following molding and printing of the breast implant shell with multiple sensor modules on the shell surface, a silicone gel is injected into the implant through an orifice at the base of the implant. Methods and materials to inject the silicone gel and to seal the orifice with siloxane elastomer are described (see e.g., U.S. Pat. No. 8,043,373 Ibid.).

A fluid transport film is fabricated to correspond to the external surface of the breast implant and configured to transport interstitial fluid from the periphery of the implant to the sensor modules on the implant shell. Fluid transport films constructed from polyolefins by molding microchannels into a polymer film are described. See, for example, U.S. Pat. No. 6,420,622 "Medical Article Having Fluid Control Film," to Johnston et al., which is incorporated herein by reference. For example, a polymer film of polypropylene is cast with replicated parallel microchannels that are rectilinear and have a width less than 1500 µm and a depth of approximately 100-1000 µm. Interstitial fluids are wicked through microchannels of the fluid transport film, collected in a manifold and directed via a connector to proximal sensor modules. Fluid transport films with microchannels, a manifold, a connector and a vacuum source are described (see e.g., U.S. Pat. No. 6,420,622, Ibid.). A fluid transport film is fabricated with microchannels to collect interstitial fluid from all surfaces of the implant shell and to deliver the fluids to sensor modules proximal to the collection sites. The fluid transport film is substantially the same shape as the implant, configured to correspond to the outer surface of the shell with a gap between the film and the outer surface of the shell. The fluid transport film is positioned around the outer surface of the shell. At least one tether may be fabricated to connect the film and the outer surface of the shell, the tether(s) adhered to both the film and the outer surface of the shell with a suitable adhesive.

Example 4

A Breast Implant System for Breast Augmentation Configured to Permit Magnetic Resonance Imaging A patient undergoes breast augmentation surgery employing a breast implant system that includes breast implant prostheses with sensor modules configured to monitor for cancer biomarkers in tissue exudates and interstitial fluids surrounding the breast implants. The breast implant system detects shed or secreted breast cancer analytes with a network of sensor modules (see, e.g. FIG. 2) distributed on the surface of the implant. The sensor modules are configured to signal wirelessly to an external receiver when interrogated by an external device including a reader. The external device including the receiver can send alerts to the patient and to the patient's physician when breast cancer analytes are detected.

The breast implant prosthesis is a gel-filled hemispherical or crescent-shaped implant including a shell. The implant includes sensor modules attached to the surface of the shell. The sensor modules are configured to detect analytes that are breast cancer markers. See Examples 1-3.

Sensor modules are fabricated containing antibody-based electrochemical sensor units, with removable covers, as described (see, e.g. U.S. Pat. No. 7,577,470, "Long Term Analyte Sensor Array," to Shah et al., which is incorporated herein by reference). Antibodies directed to specific recognition of breast cancer analytes are commercially available. For example, multiple antibodies directed to the breast cancer analyte HER-2 (also known as ErbB2) are available from R&D Systems, Minneapolis Minn. For example, multiple antibodies directed to the breast cancer analyte matrix metalloproteinase-2, or "MMP-2," are available from Novus Biologicals, Littleton, Colo. For example, antibodies directed to the breast cancer analyte CA 15-3 are available from Lee Biosolutions, St. Louis, Mo. Each sensor module includes: at least one sensor unit configured to detect HER-2 with a HER-2 specific antibody; at least one sensor unit configured to detect MMP-2 with a MMP-2 specific antibody; and at least one sensor unit configured to detect CA 15-3 with a CA 15-3 specific antibody. Each sensor module is attached to a transmission unit configured to receive signals from the sensor units when analytes are detected, and to send a signal to a remote device external to the body including the implant (see, e.g. U.S. Pat. No. 7,577,470, ibid). The sensor modules configured to detect breast cancer antigens are machined on silicon chips, and constructed with non-ferromagnetic materials (i.e., paramagnetic or diamagnetic) and/or metal alloys that are minimally affected by an external magnetic field in order to be compatible with magnetic resonance imaging (MRI).

A transmission unit is fabricated to attach to each sensor module. Each transmission unit includes at least one antenna and circuitry to receive and transmit radio frequency signals. A transmission unit can be configured to send and receive signals in the radio frequency spectrum and including a unique identifier, i.e. to be a "RFID unit." Each transmission unit includes a unique identifier to identify information from a particular sensor module on the breast implant. Methods and materials to construct transmission units with antennas, transmitters, and power harvesters are described (see e.g: U.S. Pat. No. 7,479,886, "Antenna Capacitance for Energy Storage," to Burr; and U.S. Pat. No. 7,411,505, "Switch Status and RFID Tag," to Smith et al., which are each incorporated herein by reference). Each transmission unit is fabricated from MRI-compatible materials. Transmission units constructed from non-ferromagnetic materials which are compatible with MRI studies are described (see e.g., U.S. Patent Application No. 2011/0077736, "Breast Implant System Including Bio-Medical Units," to Rofougaran and U.S. Patent Application No. 2007/0106332, "MRI Compatible Implanted Electronic Medical Device," to Denker et al. which are each incorporated herein by reference).

The sensor modules are attached to the shell of the breast implant in a uniformly distributed network. For example, a hemispherical breast implant shell with a diameter of approximately 12 cm will have a total surface area of approximately 300 $cm^2$ and can include approximately 50 to 100 sensor modules attached with their midpoints approximately 3 to 6 cm apart and uniformly distributed over the surface of the implant. The sensor modules and transmission units are attached using suitable adhesive.

The breast implant shell is filled with an elastic silicone gel. Following molding of the breast implant shell and attachment of multiple sensor modules on the shell surface, a silicone gel is injected into the implant through an orifice at the base of the implant. Methods and materials to inject the silicone gel and to seal the orifice with siloxane elastomer are described (see e.g., U.S. Pat. No. 8,043,373 Ibid.).

Sensor modules can contain multiple, replicate antibody-based sensor units which detect a set of breast cancer markers. For example, each sensor module can include approximately 70 replicate sensor units with each sensor unit detecting 3 different cancer antibodies (e.g., HER-2, MMP-2 and CA 15-3). See FIG. 13. Sensor modules containing multiple sensor units have been described (see e.g., U.S. Pat. No. 7,577,470, Ibid.). The 70 sensor units present in each sensor module can be protected with covers that can be individually removed as needed to monitor breast cancer antigens over several years. For example, the individual sensor units can be covered with membranes (e.g., thin gold foil) that protect the sensors from interstitial fluid, cells, and biofouling. When a new sensor unit is needed on a sensor module, the protective membrane over one sensor unit is removed by the application of an electric current which disrupts the gold foil cover and exposes the new sensor unit to surrounding interstitial fluid and tissues (see e.g., U.S. Pat. No. 7,577,470, Ibid.). Replicate sensor units configured to detect the same breast cancer analyte can be sequentially exposed to monitor the regions surrounding the breast cancer implant over a period of approximately 5 years. If a sensor becomes nonfunctional, i.e., no longer signals, it can be deactivated by wireless signaling from a remote device. A new sensor unit can be activated by disrupting its protective membrane and engaging circuitry to the new sensor unit.

The breast implant system including the breast implant prostheses with multiple sensor modules is used to augment the patient's breasts. After surgery, an external device is used monitor the sensor modules detection of analytes that are breast cancer markers in tissue fluids. The external device can be configured to transmit radiowaves that signal the sensor modules and provide a source of power. External devices to communicate with sensor modules are described (see e.g., U.S. Patent Appl. No. 2011/0077736, Ibid.). The external device can be a cell phone configured to receive signals from the transmission units when breast cancer analytes are detected. For example, an external device installed in the patient's home may interrogate and empower the sensor modules on the breast implants daily when the patient arrives home. The external device can be configured to control the sensor modules, such as by triggering activation of specific sensor units distributed over the surface of the breast implant shell through removal of a specific cover or set of covers. The external device can alert the patient and the patient's physician when breast cancer markers are detected, or sensor modules become dysfunctional, or the system otherwise needs attention.

Example 5

A Breast Implant System with Compartments Containing Localized Sensor Modules Configured to Detect Breast Cancer Analytes A patient has a total reconstruction of the breast employing a breast implant system. The breast implant system includes a gel-filled breast implant prosthesis including a shell (see Example 1, above). The breast implant includes external projections forming a series of compartments on the surface of the implant shell. The external projections are configured like a plurality of membranes projecting at substantially right angles from the exterior surface of the implant shell, creating a series of compartments on the shell surface. Breast implant prosthesis with membranes attached to the surface are described. See, e.g. U.S. Pat. No. 3,559,214, "Compound Prosthesis," to Pangman. The projections attached to the instant embodiment are adjacent to the outer surface of the shell. The projections can be fabricated from a similar material as the shell, and attached to the shell at approximately right angles to the shell surface. The projections are substantially planar sheets of soft, bio-compatible material attached to the exterior surface of the shell with a suitable adhesive. The projections form a series of compartments adjacent to the surface. Each compartment has a depth approximately equivalent to the height of the projections forming the compartment. The projections are approximately 2 to approximately 10 mm in height, as measured from the surface of the shell to the distal edge of the projection.

Figure 14:
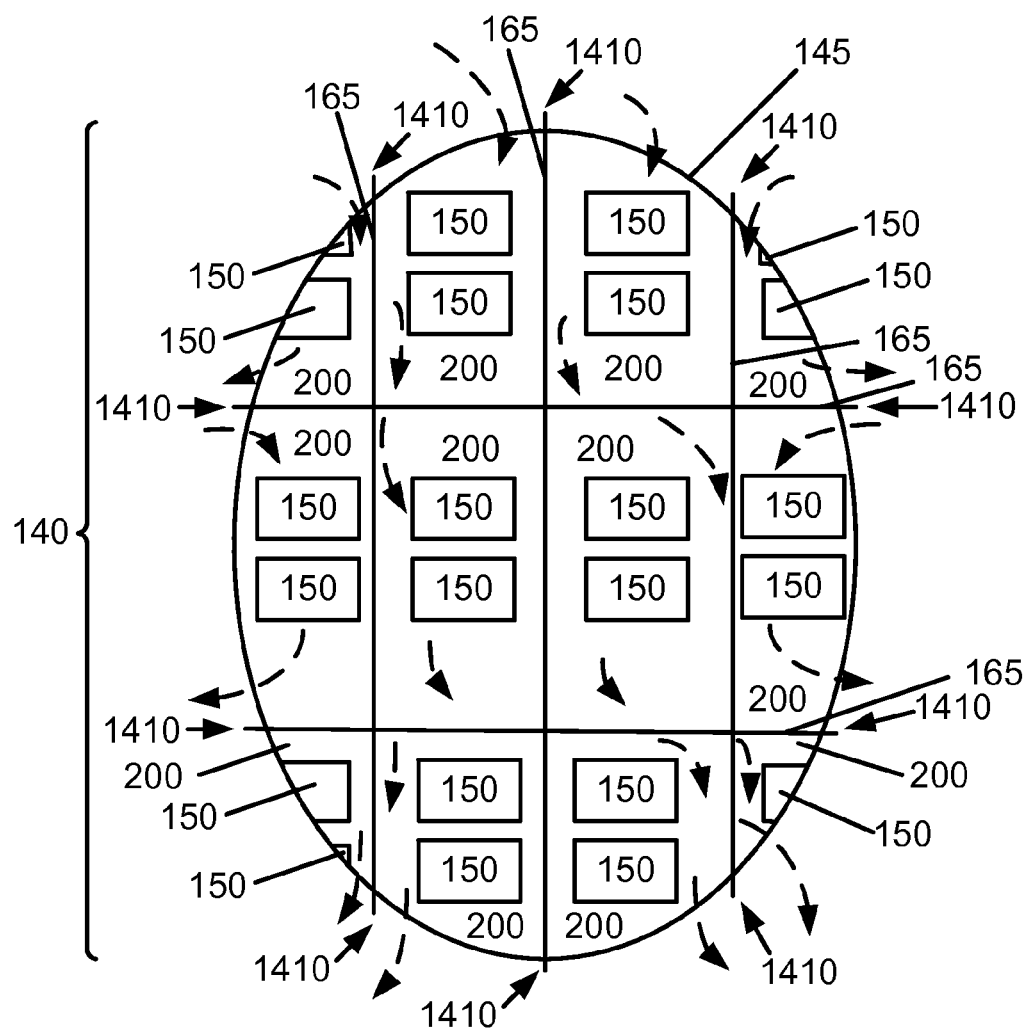
FIG. 14 is a schematic of a breast implant ex vivo in cross-section view.

For example, FIG. 14 illustrates a breast implant 140 including a shell 145. The view illustrated in FIG. 14 is an external, frontal view of a breast implant 140 ex-vivo. The exterior of the shell 145 includes a plurality of projections 1400 extending at substantially right angles from the face of the external surface of the shell 145. The projections 1400 are substantially planar, sheet-like projections. Since the breast implant 140 is depicted in a frontal view, the projections 1400 are depicted as lines over the surface of the shell 145. The projections 1400 continue beyond the surface of the shell 145, which is illustrated 1410. The plurality of projections 1400 form a series of compartments 1420 on the surface of the shell 145. Each of the compartments 1420 includes sensor modules 150. In the illustration shown in FIG. 14, each compartment 1420 includes two sensor modules 150. The compartments 1420 are substantially rectangular with their long axis oriented approximately vertically relative to the expected position of the breast implant 140 in vivo. This position facilitates gravity enhancing the flow of interstitial fluid from the top to the bottom through each compartment 1420 when the breast implant 140 is in situ (see dotted arrows).

Each compartment includes at least one long-lived sensor module configured to monitor the tissues surrounding the implant, more specifically those adjacent to the compartment, for analytes indicating any new or recurrent breast cancers that may arise. Each compartment includes at least one transmission unit attached to a sensor module. See Example 2 for a description of the sensor modules and attached transmission units. Sensor modules and transmission units are attached to the shell of the breast implant within the compartments and configured to monitor the interstitial fluids entering each compartment. For example, a hemispherical breast implant shell with a diameter of approximately 12 cm and a total surface area of approximately 300 cm$^2$ can include approximately 15 compartments with each circumscribing approximately 20 cm$^2$. Each compartment can contain 1-3 sensor modules to monitor the region proximal to the compartment. The implant can include a total of approximately 30-45 sensor modules to monitor interstitial fluids from tissues surrounding the breast implant. Each sensor module and transmission unit is attached to the surface of the shell with a suitable adhesive in a compartment region formed between the projections. See FIG. 14.

Following molding of the breast implant shell with exterior partitions and attachment of multiple sensor modules on the shell surface, a silicone gel is injected into the implant through an orifice at the base of the implant. Methods and materials to inject the silicone gel and to seal the orifice with siloxane elastomer are described (see e.g., U.S. Pat. No. 8,043,373 Ibid.).

The breast implant system including the breast implant prosthesis with compartments containing sensor modules and transmission units is used to reconstruct the patient's breast. Over time, the implant and an external, remote device is used to monitor tissue exudates and interstitial fluids for analytes that are breast cancer biomarkers. The implant system includes an external, remote device with a receiver operable to receive transmissions from the transmission units and a display that can be activated to alert the patient and medical personnel if the analytes are detected. The external, remote device can be a cell phone configured to receive signals from the transmission units. The external, remote device can be configured to send signals that control the sensor modules, such as by triggering activation of specific sensor units distributed over the surface of the breast implant shell through removal of a specific cover or set of covers. The external, remote device can alert the patient and the patient's physician when breast cancer analytes are detected, or sensor modules become dysfunctional, or the system needs attention.

Example 6

A Breast Implant System with Compartments Containing Localized Sensor Modules Configured to Permit Magnetic Resonance Imaging A patient undergoes breast augmentation surgery employing a breast implant system. The breast implants include projections forming compartments, as described in Example 5. Attached to the surface of the shell within each compartment is at least one sensor module and an attached transmission unit configured to harvest operating power from incoming RF signals. See Example 4. The transmission units each include an identification code specific to that unit. The transmission units are configured to signal wirelessly to an external receiver when interrogated by remote device. The remote device includes a display to alert the patient and the patient's physician when breast cancer analytes are detected.

The breast implant system is fabricated to be MRI-compatible. The breast implant shell, projections and interior viscous material are selected to be MRI-compatible. In addition, each sensor module and attached transmission unit is fabricated from MRI-compatible materials. See e.g., U.S. Patent Application No. 2011/0077736, "Breast Implant System Including Bio-Medical Units," to Rofougaran and U.S. Patent Application No. 2007/0106332, "MRI Compatible Implanted Electronic Medical Device," to Denker et al. which are each incorporated herein by reference. For example, the implanted system, including sensor units and transmission units, can be fabricated from non-ferromagnetic materials. For example, the electrical connections of the sensor modules and attached transmission units can be made with silica or plastic based fibers.

Following molding of the breast implant shell with exterior partitions and attachment of multiple sensor modules on the shell surface, a silicone gel is injected into the implant through an orifice at the base of the implant. Methods and materials to inject the silicone gel and to seal the orifice with siloxane elastomer are described (see e.g., U.S. Pat. No. 8,043,373 Ibid.).

The breast implant shell is encased in at least one fluid transport film to enclose the compartments on their outer sides, distal to the surface of the shell. The film is configured to promote fluid flow into the compartments from the adjacent tissue region. Following molding of the breast implant shell with exterior projections and attachment of multiple sensor modules and transmission units on the shell surface, a fluid transport film is fabricated to enclose the compartments on the breast implant shell. The fluid transport film is configured to transport interstitial fluid into the compartments and into proximity with the sensor modules. Fluid transport films constructed from polyolefins by molding microchannels into a polymer film are described (see e.g, U.S. Pat. No. 6,420,622 "Medical Article Having Fluid Control Film," to Johnston et al., which is incorporated herein by reference). For example, a polymer film of polypropylene can be cast with replicated parallel microchannels which are rectilinear with a width less than 1500 μm and a depth of approximately 100-1000 μm. Interstitial fluids are wicked through microchannels of the fluid transport film, collected in a manifold and directed via a connector to proximal sensor modules. The fluid transport film is substantially the same shape as the implant, configured to correspond to the outer surface of the shell with a gap between the film and the outer surface of the shell. The fluid transport film is positioned around the outer surface of the shell. At least one tether may be fabricated to connect the film and the outer surface of the shell, the tether(s) adhered to both the film and the outer surface of the shell with a suitable adhesive. The implant can also be enveloped with coatings to reduce encapsulation of the implant and to promote vascularization of the surrounding tissue (see above Examples).

Example 7

A Breast Implant System Harvesting Optical Power

A patient with breast cancer undergoes a total mastectomy of the affected breast, and after suitable medical treatment the breast is reconstructed with a breast implant system. The breast implant system includes a gel-filled breast implant and multiple attached long-lived sensor modules configured to monitor the tissues surrounding the implant for any new or recurrent breast cancers that may arise. See Example 2. The long lived sensor modules can detect analytes that are breast cancer markers and report the detection via attached transmission units. The long lived sensor modules are each operably attached to an optical power collector affixed to the shell. An optical power converter attached to each sensor module converts harvested optical power into electrical power for the sensor module and attached transmission unit. The implant system also includes a remote device with an external receiver configured to receive transmissions from the implant and to alert the patient and medical personnel if breast cancer analytes are detected.

Multiple analyte sensor modules are attached to the surface of the breast implant shell and configured to detect analytes associated with breast cancer. The implant also includes at least one optical power collector configured to harvest optical energy and a series of optical fibers connecting the optical power collector to optical power converters attached to each sensor module. The breast implant prosthesis shell with attached sensor modules and attached transmission units is fabricated as described in Example 2, with the exception that each of the attached sensor modules and attached transmission units also includes an attached optical power converter configured to convert the transmitted optical power into electrical energy to power the sensor modules and attached transmission units. See e.g.: U.S. Patent Appl. 2011/0044694, "Systems and Methods for Optically Powering Transducers and Related Transducers," to Scherer et al.; US Patent Application No. 2010/0070003, "Systems configured to power at least one device disposed in a living subject, and related apparatuses and methods," to Hyde et al.; and Ayazian et al., "Delivering Optical Power to Subcutaneous Implanted Devices," *Conf Proc. IEEE Eng. Med. Biol. Soc.* 2011: 2874-2877 (2011), which are each incorporated herein by reference. Each optical power converter is configured to receive optical power from an optical power collector through an optic fiber attached to both the optical power collector and the power converter.

Sensor modules are empowered by an optical power converter that supplies electric current to the sensor module. Optically powered transducers and converters suitable for medical implants have been described (see e.g.: U.S. Patent Appl. 2011/0044694, "Systems and Methods for Optically Powering Transducers and Related Transducers," to Scherer et al.; US Patent Application No. 2010/0070003, "Systems configured to power at least one device disposed in a living subject, and related apparatuses and methods," to Hyde et al.; and Ayazian et al., "Delivering Optical Power to Subcutaneous Implanted Devices," *Conf. Proc. IEEE Eng. Med. Biol. Soc.* 2011: 2874-2877 (2011), which are each incorporated herein by reference). For example, a photovoltaic collector and electronic circuitry can be fabricated using a standard CMOS (Complementary metal-oxide-semiconductor) process in a silicon foundry. A photovoltaic collector irradiated with 10 mW/cm$^2$ of light input power yields approximately 3.1 mW/cm$^2$ power output, i.e., an efficiency of about 31%. The optical power collector is attached to an outer surface of the implant shell with suitable adhesive. The optical power collector(s) are attached to an outer surface of the implant shell at a location where minimal tissue is expected to be positioned between the optical power collector and the exterior skin surface of the patient. For example, the optical power collector is attached to an outer surface of the implant shell at a location expected to correspond with the front region of the patient's breast.

During medical exams, the optical power collectors are irradiated by an optical reader that generates optical energy with a near-IR semiconductor laser using a wavelength between approximately 680 nm and 980 nm. An external optical reader with a near IR laser can provide optical energy to the implant optical power collectors through as much as several centimeters of tissue. The optical reader, an external component of the breast implant system, can be periodically utilized to empower the sensor modules and attached transmission units, such as during medical visits, to monitor the breast implant for the potential detection of breast cancer analytes.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

With respect to the appended claims, the recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A breast implant comprising:
    a shell configured to be substantially filled with a viscous material;
    a plurality of projections extending from an external surface of the shell, each of the plurality of projections including a first end surface sealed to the external surface of the shell, the projections forming a plurality of compartments adjacent to the external surface of the shell;
    at least one fluid-permeable cover attached to the projections, each of the plurality of projections including a second end surface sealed to a surface of the cover, the cover completely enveloping the shell and the plurality of projections;
    a plurality of sensor modules attached to the shell, each of the sensor modules positioned within one of the plurality of compartments, wherein each of the plurality of sensor modules includes a unique identifier; and
    at least one power source operably attached to the plurality of sensor modules.

2. The breast implant of claim 1, wherein the plurality of compartments comprise:
    a region of the at least one fluid-permeable cover forming a side of each of the compartments, the region including at least one set of influx microchannels configured to direct the fluid into the compartment, and including at least one set of efflux microchannels configured to direct the fluid out of the compartment.

3. The breast implant of claim 1, wherein the at least one fluid-permeable cover comprises:
    a mesh structure.

4. The breast implant of claim 1, wherein the at least one fluid-permeable cover comprises:
    an analyte-permeable cover.

5. The breast implant of claim 1, wherein the at least one fluid-permeable cover comprises:
    a porous structure.

6. The breast implant of claim 1, wherein the plurality of sensor modules attached to the shell comprise:
    at least one sensor module configured to detect at least two analytes in the fluid within a compartment, wherein the at least two analytes are of different types.

7. The breast implant of claim 1, wherein the plurality of sensor modules attached to the shell comprise:
    at least two sensor types in each sensor module.

8. The breast implant of claim 1, wherein the plurality of sensor modules attached to the shell are configured to detect one or more biological analytes arising from biological tissue.

9. The breast implant of claim 1, wherein the plurality of sensor modules are configured to be rechargeable.

10. The breast implant of claim 1, wherein the unique identifier for each of the plurality of sensor modules comprises:
    an alphanumeric code.

11. The breast implant of claim 1, wherein the unique identifier for each of the plurality of sensor modules comprises:
    a positional identifier.

12. The breast implant of claim 1, wherein the at least one power source is configured to be rechargeable.

13. A breast implant comprising:
    a shell configured to be substantially filled with a viscous material;
    a plurality of projections extending from an external surface of the shell, each of the plurality of projections including a first end surface sealed to the external surface of the shell, the projections forming a plurality of compartments adjacent to the external surface of the shell;
    at least one fluid-permeable cover attached to the projections, each of the plurality of projections including a second end surface sealed to a surface of the cover, the cover completely enveloping the shell and the plurality of projections;
    a plurality of sensor modules attached to the shell, each of the sensor modules positioned within one of the plurality of compartments, wherein each of the plurality of sensor modules includes a unique identifier;
    at least one processor operably attached to the plurality of sensor modules; and
    at least one power source operably attached to the at least one processor.

14. The breast implant of claim 13, wherein the plurality of compartments comprise:
    a region of the at least one fluid-permeable cover forming a side of each of the compartments, the region including at least one set of influx microchannels configured to direct the fluid into the compartment, and including at least one set of efflux microchannels configured to direct the fluid out of the compartment.

15. The breast implant of claim 13, wherein the at least one fluid-permeable cover comprises:
    an analyte-permeable cover.

16. The breast implant of claim 13, wherein the at least one fluid-permeable cover comprises:
    a porous structure.

17. The breast implant of claim 13, wherein the plurality of sensor modules attached to the shell comprise:
    at least one sensor module configured to detect at least two analytes in the fluid within a compartment, wherein the at least two analytes are of different types.

18. The breast implant of claim 13, wherein the plurality of sensor modules attached to the shell comprise:
    at least two sensor types in each sensor module.

19. The breast implant of claim 13, wherein the plurality of sensor modules attached to the shell are configured to detect one or more biological analytes arising from biological tissue.

20. The breast implant of claim 13, wherein the plurality of sensor modules are configured to be rechargeable.

21. The breast implant of claim 13, wherein the unique identifier for each of the plurality of sensor modules comprises:
    an alphanumeric code.

22. The breast implant of claim 13, wherein the unique identifier for each of the plurality of sensor modules comprises:
a positional identifier.

23. The breast implant of claim 13, wherein the at least one power source is configured to be rechargeable.

24. A breast implant comprising:
a shell configured to be substantially filled with a viscous material;
a plurality of projections extending from an external surface of the shell, each of the plurality of projections including a first end surface sealed to the external surface of the shell, the projections forming a plurality of compartments adjacent to the external surface of the shell;
at least one fluid-permeable cover attached to the projections, each of the plurality of projections including a second end surface sealed to a surface of the cover, the cover completely enveloping the shell and the plurality of projections;
a plurality of sensor modules attached to the shell, each of the sensor modules positioned within one of the plurality of compartments, wherein each of the plurality of sensor modules includes a unique identifier;
at least one processor operably attached to the plurality of sensor modules;
at least one power source operably attached to the at least one processor; and
at least one transmission unit operably attached to the at least one processor.

25. The breast implant of claim 24, wherein the plurality of compartments comprise:
a region of the at least one fluid-permeable cover forming a side of each of the compartments, the region including at least one set of influx microchannels configured to direct the fluid into the compartment, and including at least one set of efflux microchannels configured to direct the fluid out of the compartment.

26. The breast implant of claim 24, wherein the at least one fluid-permeable cover comprises:
a mesh structure.

27. The breast implant of claim 24, wherein the at least one fluid-permeable cover comprises:
an analyte-permeable cover.

28. The breast implant of claim 24, wherein the at least one fluid-permeable cover comprises:
a porous structure.

29. The breast implant of claim 24, wherein the plurality of sensor modules attached to the shell comprise:
at least one sensor module configured to detect at least two analytes in the fluid between the shell and the cover, wherein the at least two analytes are of different types.

30. The breast implant of claim 24, wherein the plurality of sensor modules attached to the shell comprise:
at least two sensor types in each sensor module.

31. The breast implant of claim 24, wherein the plurality of sensor modules attached to the shell are configured to detect one or more biological analytes arising in biological tissue.

32. The breast implant of claim 24, wherein the plurality of sensor modules are configured to be rechargable.

33. The breast implant of claim 24, wherein the unique identifier for each of the plurality of sensor modules comprises:
an alphanumeric code.

34. The breast implant of claim 24, wherein the unique identifier for each of the plurality of sensor modules comprises:
a positional identifier.

35. The breast implant of claim 24, wherein the at least one power source is configured to be rechargeable.

36. The breast implant of claim 24, wherein the at least one transmission unit comprises:
a radio-frequency transmitter.

37. The breast implant of claim 24, wherein the at least one transmission unit comprises:
an infrared transmitter.

38. A breast implant comprising:
a shell configured to be substantially filled with a viscous material;
a plurality of projections extending from an external surface of the shell, each of the plurality of projections including a first end surface sealed to the external surface of the shell, the projections forming a plurality of compartments adjacent to the external surface of the shell;
a plurality of sensor modules attached to the shell, each of the sensor modules positioned within one of the plurality of compartments;
at least one transmission unit attached to the plurality of sensor modules; and
at least one power source attached to the plurality of sensor modules and to the transmission unit.

39. The breast implant of claim 38, wherein the plurality of sensor modules are positioned on the shell with a distance between the sensor modules.

40. The breast implant of claim 38, comprising:
at least one switch attached to both the at least one transmission unit and the plurality of sensor modules, the at least one switch configured to activate the transmission unit in response to a signal from one or more of the sensor modules.

* * * * *